United States Patent
Burke et al.

(10) Patent No.: US 9,533,999 B2
(45) Date of Patent: Jan. 3, 2017

(54) FUSED THIAZIN-3-ONES AS KCA3.1 INHIBITORS

(71) Applicant: Boehringer Ingelheim International GmbH, Ingelheim am Rhein (DE)

(72) Inventors: Michael J. Burke, Newtown, CT (US); Bryan McKibben, New Milford, CT (US); Matt Aaron Tschantz, Newtown, CT (US)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 257 days.

(21) Appl. No.: 14/434,671

(22) PCT Filed: Jun. 12, 2013

(86) PCT No.: PCT/US2013/045405
§ 371 (c)(1),
(2) Date: Apr. 9, 2015

(87) PCT Pub. No.: WO2013/191984
PCT Pub. Date: Dec. 27, 2013

(65) Prior Publication Data
US 2015/0232484 A1    Aug. 20, 2015

Related U.S. Application Data

(60) Provisional application No. 61/662,632, filed on Jun. 21, 2012.

(51) Int. Cl.
*C07D 513/04*    (2006.01)

(52) U.S. Cl.
CPC .................. *C07D 513/04* (2013.01)

(58) Field of Classification Search
CPC ................................................ C07D 513/04
USPC ......................................... 514/224.2; 544/48
See application file for complete search history.

(56) References Cited

U.S. PATENT DOCUMENTS

2010/0056637 A1    3/2010    Castle et al.

FOREIGN PATENT DOCUMENTS

| WO | 9726264 A1 | 7/1997 |
| WO | 0055147 A1 | 9/2000 |
| WO | 2012006117 A2 | 1/2012 |

OTHER PUBLICATIONS

Jamoulle, J. C. Journal de Pharmacie de Belgique (1978), 33(5), 277-83.*
International Search Report and Written Opinion for PCT/US2013/045405 mailed Jul. 24, 2013.
Prasad, R. N. et al.., "Chemistry and Synthesis of Some Dihydro-2H-1,4-Benzothiazine Derivatives." Canadian Journal of Chemistry, 1966, vol. 44, No. 11, pp. 1247-1258.
Takamizawa, A. et al., "Studies on Pyrimidine Derivatives and Related Compounds. XCIV. On the Oxidation Products of 2-Substituted-2,3-dihydro-4H-1,4-thiazin-3-one Derivatives." Chemical and Pharmaceutical Bulletin, 1980, vol. 28, No. 3, pp. 769-778.

* cited by examiner

*Primary Examiner* — Kahsay Habte
(74) *Attorney, Agent, or Firm* — Michael P. Morris; Atabak R. Royaee

(57) ABSTRACT

The present invention encompasses compounds of the formulas (I) & (II), wherein the groups A, L and Ar are defined as in claim 1, which are suitable for the treatment of diseases related to KCa3.1, process of making, pharmaceutical preparations which contain compounds and their methods of use.

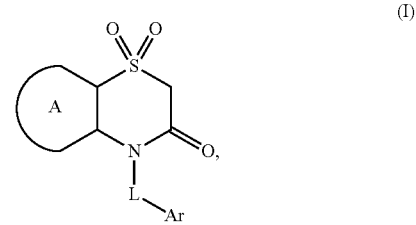

(I)

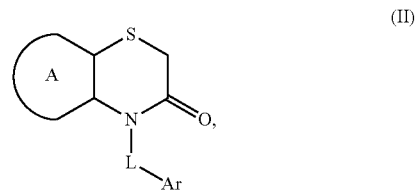

(II)

28 Claims, No Drawings

FUSED THIAZIN-3-ONES AS KCA3.1 INHIBITORS

BACKGROUND OF THE INVENTION

1. Technical Field

The present invention relates to novel compounds which inhibit the KCa3.1 and their use as medicaments.

2. Background Information

KCa3.1, also known as KCNN4, SK4, IKCa1, IK1 and Gardos channel, is an intermediate-conductance potassium-ion channel which is activated by intracellular calcium (1). The C-terminal calmodulin domain of KCa3.1 serves as a sensor for intracellular $[Ca^{2+}]$ and regulates $Ca^{2+}$-mediated channel opening via cross-linking of subunits in the channel tetramer (2). Activation of KCa3.1 by elevated intracellular $Ca^{2+}$ maintains a negative membrane potential through efflux of $K^+$, which helps to sustain $Ca^{2+}$ entry into the cell. KCa3.1 is expressed in a variety of cell types including T cell, B cell, macrophage, microglial cell, mast cell, red blood cell, fibroblast, vascular smooth muscle cell and epithelial cell. Thus, KCa3.1 plays an important function in regulating $Ca^{2+}$ influx—mediated functions such as cytokine production, proliferation and migration in these cells. In T cells, sustained $Ca^{2+}$ influx via the CRAC channel is important for sufficient cytokine production and proliferation. T-cell receptor engagement dramatically induces KCa3.1 expression, in parallel with increased KCa3.1 currents and enhanced $[Ca^{2+}]_i$ signaling during human T-cell activation (3). KCa3.1 deficiency leads to decreased TCR-stimulated $Ca^{2+}$ influx and cytokine production in mouse Th0, Th1, and Th2 cells (7). KCa3.1$^{-/-}$ mice are protected from developing severe colitis in two models of inflammatory bowel disease (IBD) (4), suggesting that KCa3.1 inhibitors could be beneficial for inflammatory bowel diseases such as Crohn's disease and ulcerative colitis. In addition to IBD, KCa3.1 is also a potential target for several other disease indications including atherosclerosis, multiple sclerosis, rheumatoid arthritis, asthma, renal fibrosis, diabetes and sickle cell anemia. KCa3.1 inhibitors TRAM-34 and clotrimazole significantly reduces the development of atherosclerosis in aortas of ApoE$^{-/-}$ mice (5). TRAM-34 also inhibits in an experimental autoimmune encephalomyelitis (EAE) model induced by MOG35-55 peptide in C57BL/6 mice (6). KCa3.1 deficient mice show improved glucose homeostasis (through pancreatic beta cells) without affecting insulin sensitivity, suggesting KCa3.1 is a potential target for type II diabetes (7). In addition, KCa3.1 plays an important role in proliferation of renal fibroblasts, and KCa3.1 deficient mice or TRAM-34 treated mice show attenuated progression of renal fibrosis induced by unilateral ureteral obstruction (UUO) (7), indicating that KCA3.1 may serve as a therapeutic target for fibrotic kidney disease. Pharmacological KCa3.1 blockade reduced erythrocyte dehydration in both a mouse model of sickle-cell anemia and in patients with the disease (8). Taken together, a KCa3.1 inhibitor potentially will have therapeutic values for multiple disease indications.

REFERENCE LIST

1. H. Wulff, C. Beeton, K. G. Chandy, *Curr Opin Drug Discov Devel.* 6, 640 (2003).
2. M. A. Schumacher, A. F. Rivard, H. P. Bachinger, J. P. Adelman, *Nature* 410, 1120 (2001).
3. S. Ghanshani et al., *J Biol. Chem.* 275, 37137 (2000).
4. L. Di et al., *Proc Natl Acad Sci USA* 107, 1541 (2010).
5. K. Toyama et al., *J Clin Invest* 118, 3025 (2008).
6. E. P. Reich et al., *Eur J Immunol* 35, 1027 (2005).
7. I. Grgic et al., *Proc Natl Acad Sci USA* 106, 14518 (2009).
8. K. I. Ataga, J. Stocker, *Expert Opin Investig. Drugs* 18, 231 (2009).

SUMMARY OF THE INVENTION

The invention comprises a novel class of fused thiazin-3-one compounds and methods for making and using the same. These compounds are useful for the treatment disease characterized by inflammation and/or bone erosion in that they exhibit good inhibitory effect upon KCa3.1.

DETAILED DESCRIPTION OF THE INVENTION

The present invention therefore relates to compounds of formula (I)

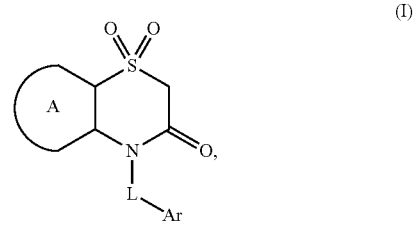

wherein
ring A

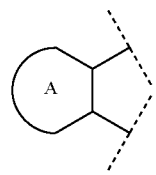

is fused to the 1,1-dioxothiazinone ring and chosen from

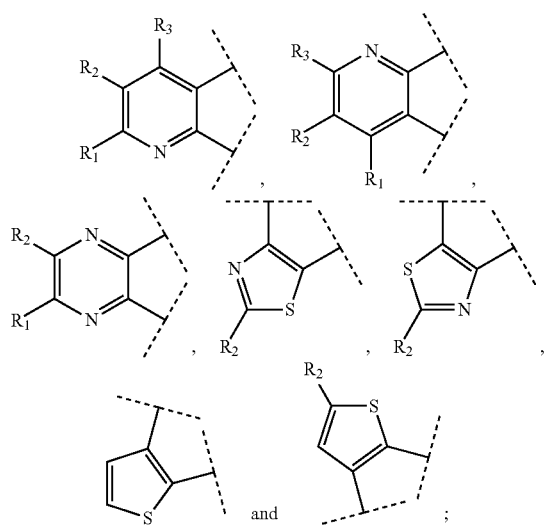

L is a bond or —(CH$_2$)$_n$— wherein one or more methylene hydrogens is optionally replaced by C$_{1-5}$alkyl, C$_{2-6}$alkenyl, C$_{2-6}$alkynyl or C$_{1-5}$haloalkyl;

n is 1 to 3;

Ar is aryl or heteroaryl substituted independently by one or more halogen, C$_{1-6}$haloalkyl, C$_{1-6}$haloalkoxy or C$_{1-6}$haloalkylS(O)$_m$— and Ar is optionally further substituted by C$_{1-6}$alkyl;

m is 0, 1 or 2;

each R$^1$, R$^2$ and R$^3$ independently chosen from hydrogen, halogen, C$_{1-5}$alkyl, C$_{3-6}$cycloalkyl, C$_{1-5}$alkyl-OH, —C(O)OR$^4$, —C(O)NR$^4$R$^4$, C$_{2-6}$alkenyl, C$_{2-6}$alkynyl, C$_{1-5}$haloalkyl, —OR$^4$, —NR$^4$R$^4$, —CN, —SR$^4$, —S(O)$_2$R$^4$, —S(O)$_2$NR$^4$R$^4$, —NHC(O)R$^4$ and —N(C$_{1-4}$alkyl)C(O)OR$^4$;

each R$^4$ is independently hydrogen, or C$_{1-6}$alkyl;

or a pharmaceutically acceptable salt thereof.

In another embodiment of the invention there is provided a compound according to the previous formula (I) embodiment and wherein L is a bond or —(CH$_2$)$_n$— wherein one or two methylene hydrogens is optionally replaced by C$_{1-3}$alkyl;

n is 1 or 2;

Ar is phenyl or heteroaryl chosen from furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl, each Ar is substituted independently by one or more halogen, C$_{1-5}$haloalkyl, C$_{1-5}$haloalkoxy or C$_{1-5}$haloalkylS(O)$_m$— and Ar is optionally further substituted by C$_{1-3}$alkyl;

m is 2;

each R$^1$, R$^2$ and R$^3$ are independently chosen from hydrogen, halogen, C$_{1-3}$alkyl, C$_{3-5}$cycloalkyl, C$_{1-3}$alkyl-OH, —C(O)OR$^4$, and —C(O)NR$^4$R$^4$;

each R$^4$ is independently hydrogen or C$_{1-3}$alkyl;

or a pharmaceutically acceptable salt thereof.

In another embodiment of the invention there is provided a compound according to the any of the formula (I) embodiments hereinabove and wherein L is a bond or —(CH$_2$)$_n$— wherein one methylene hydrogen is optionally replaced by methyl;

n is 1 or 2;

Ar is phenyl or heteroaryl chosen from pyrazolyl, and pyridyl, each Ar is substituted independently by one or more halogen, C$_{1-3}$haloalkyl, C$_{1-3}$haloalkoxy or C$_{1-3}$haloalkylS(O)$_m$— and Ar is optionally further substituted by C$_{1-3}$alkyl;

m is 2;

each R$^1$, R$^2$ and R$^3$ independently ndependently chosen from hydrogen, halogen, C$_{1-3}$alkyl, C$_{3-5}$cycloalkyl, C$_{1-3}$alkyl-OH, —C(O)OR$^4$, and —C(O)NR$^4$R$^4$;

each R$^4$ is independently hydrogen or C$_{1-3}$alkyl;

or a pharmaceutically acceptable salt thereof.

In another embodiment of the invention there is provided a compound according to the any of the formula (I) embodiments hereinabove and wherein Ar is phenyl or heteroaryl chosen from pyrazolyl, and pyridyl, each Ar is substituted independently by one or more Cl, F, Br, CF$_3$, —OCF$_3$ or —S(O)$_2$—CF$_3$ and Ar is optionally further substituted by methyl;

each R$^1$, R$^2$ and R$^3$ are independently chosen from hydrogen, halogen, C$_{1-3}$alkyl, C$_{3-5}$cycloalkyl, C$_{1-3}$alkyl-OH, —C(O)OR$^4$, and —C(O)NR$^4$R$^4$;

each R$^4$ is independently hydrogen or methyl;

or a pharmaceutically acceptable salt thereof.

In another embodiment of the invention there is provided a compound according to the any of the formula (I) embodiments hereinabove and wherein ring A

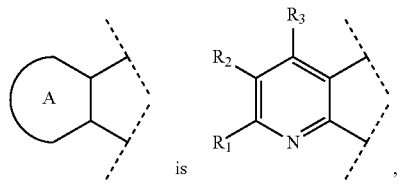

R$^1$ is hydrogen, —C(O)$_2$—CH$_3$, —C(O)—N(CH$_3$)$_2$ or —C(O)—NH$_2$;

R$^2$ is hydrogen or Cl;

R$^3$ is hydrogen;

or a pharmaceutically acceptable salt thereof.

In another embodiment of the invention there is provided a compound according to the any of the formula (I) embodiments hereinabove and wherein ring A

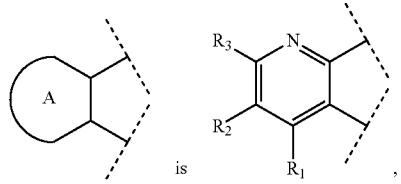

R$^1$ is hydrogen;

R$^2$ is Br;

R$^3$ is hydrogen;

or a pharmaceutically acceptable salt thereof.

In another embodiment of the invention there is provided a compound according to the any of the formula (I) embodiments hereinabove and wherein ring A

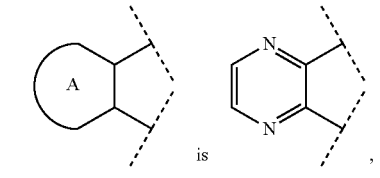

Ar is phenyl substituted independently by one or two F, CF$_3$ or —OCF$_3$;

or a pharmaceutically acceptable salt thereof.

In another embodiment of the invention there is provided a compound according to the any of the formula (I) embodiments hereinabove and wherein ring A

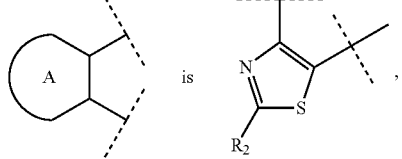

R$_2$ is hydrogen, methyl or cyclopropyl.

or a pharmaceutically acceptable salt thereof.

In another embodiment of the invention there is provided a compound according to the any of the formula (I) embodiments hereinabove and wherein
ring A

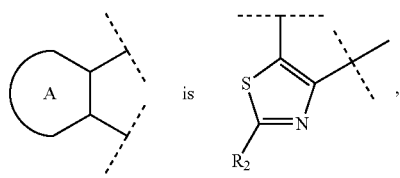

$R_2$ is hydrogen, methyl or isopropyl;
or a pharmaceutically acceptable salt thereof.

In another embodiment of the invention there is provided a compound according to the any of the formula (I) embodiments hereinabove and wherein
ring A

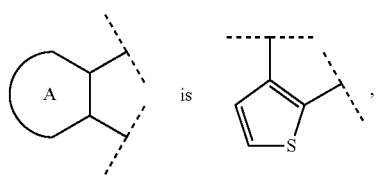

or a pharmaceutically acceptable salt thereof.

In another embodiment of the invention there is provided a compound according to the any of the formula (I) embodiments hereinabove and wherein
ring A

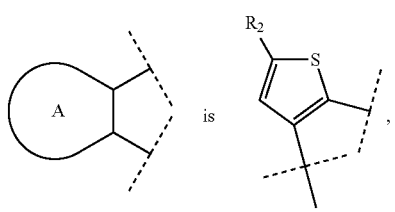

$R_2$ is hydrogen or —$CO_2$—$CH_3$,
or a pharmaceutically acceptable salt thereof.

In another embodiment of the invention there is provided a compound according to the any of the formula (I) embodiments hereinabove and wherein the combination of L-Ar is

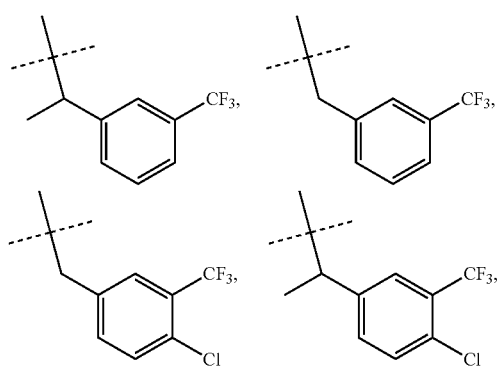

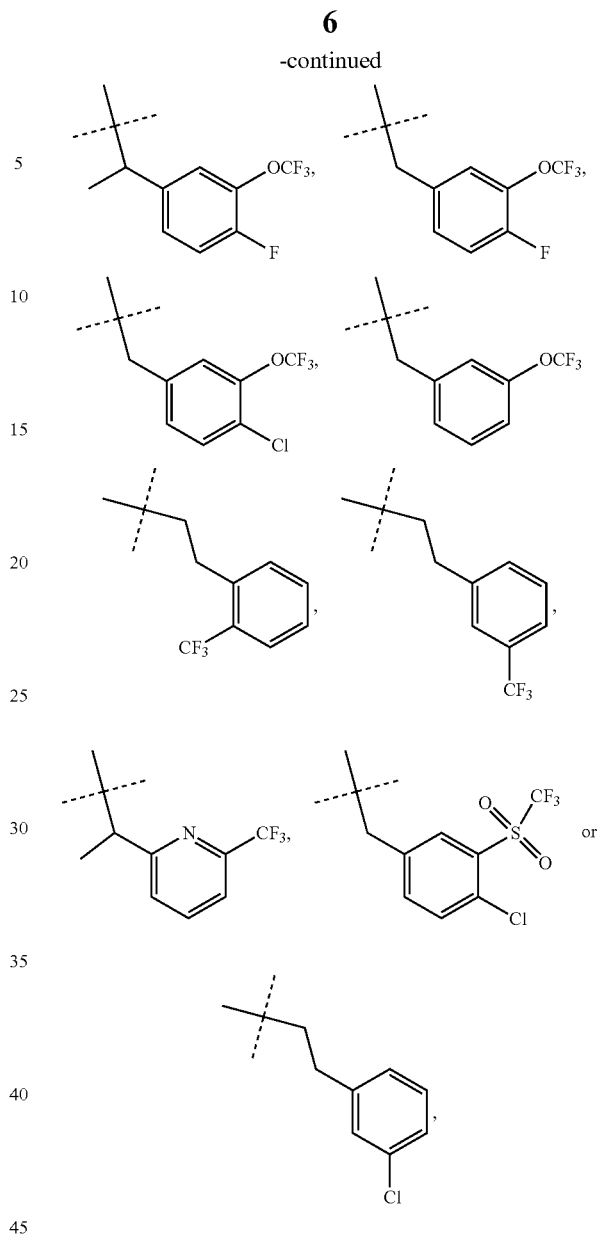

or a pharmaceutically acceptable salt thereof.

In another embodiment of the invention there is provided a compound according to the any of the formula (I) embodiments hereinabove and wherein the combination of L-Ar is

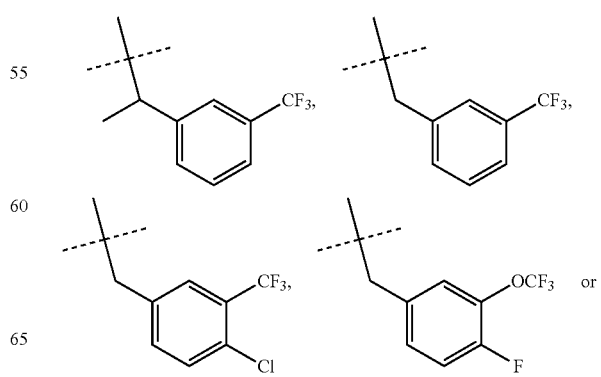

-continued

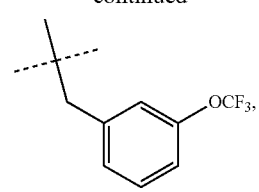

or a pharmaceutically acceptable salt thereof.

In another embodiment of the invention there is provided a compound according to the any of the formula (I) embodiments hereinabove and wherein the combination of L-Ar is

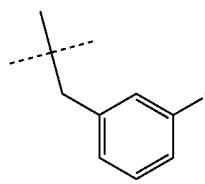 or 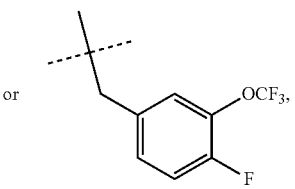

or a pharmaceutically acceptable salt thereof.

In another embodiment, the invention provides made compounds in Table I which can be made in view of the general schemes, examples and methods known in the art.

TABLE I

| Compound number | Structure |
|---|---|
| I-1 | 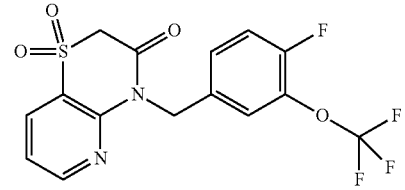 [SMILES: O=C1CS(=O)(=O)c2cccnc2N1Cc1ccc(F)c(OC(F)(F)F)c1] |
| I-2 | 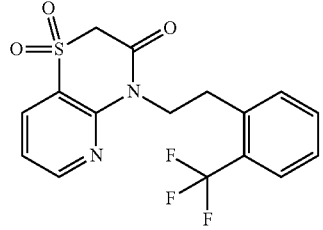 [SMILES: O=C1CS(=O)(=O)c2cccnc2N1CCc1ccccc1C(F)(F)F] |
| I-3 | 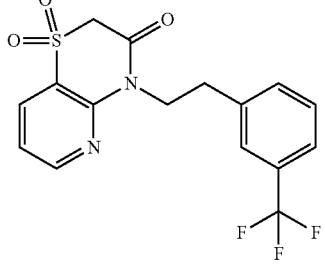 |
| I-4 | 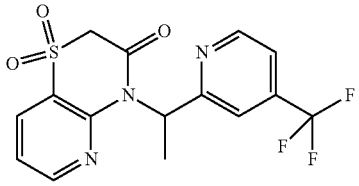 [SMILES: CC(c1cc(C(F)(F)F)ccn1)N1C(=O)CS(=O)(=O)c2cccnc21] |

TABLE I-continued

| Compound number | Structure |
|---|---|
| I-5 | 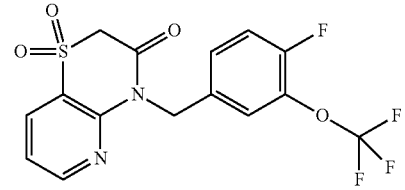 [SMILES: O=C1CS(=O)(=O)c2cccnc2N1Cc1ccc(F)c(OC(F)(F)F)c1] |
| I-6 | 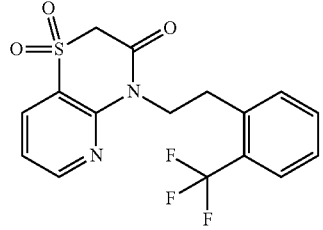 [SMILES: O=C1CS(=O)(=O)c2cccnc2N1CCc1ccccc1C(F)(F)F] |
| I-7 | 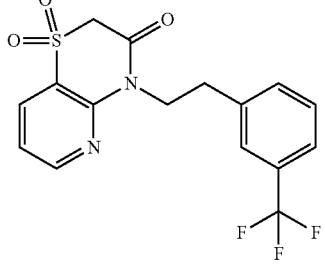 |
| I-8 | 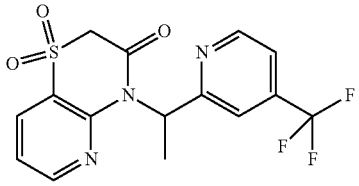 [SMILES: CC(c1cc(C(F)(F)F)ccn1)N1C(=O)CS(=O)(=O)c2cccnc21] |
| I-9 | 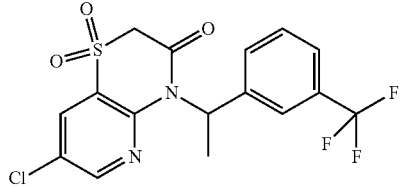 [SMILES: CC(c1cccc(C(F)(F)F)c1)N1C(=O)CS(=O)(=O)c2cc(Cl)cnc21] |
| I-10 | 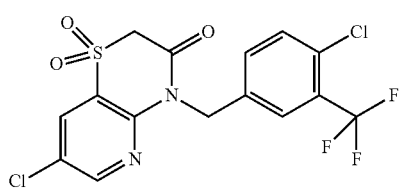 [SMILES: O=C1CS(=O)(=O)c2cc(Cl)cnc2N1Cc1ccc(Cl)c(C(F)(F)F)c1] |
| I-12 | 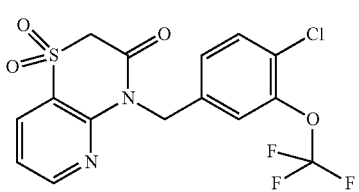 [SMILES: O=C1CS(=O)(=O)c2cccnc2N1Cc1ccc(Cl)c(OC(F)(F)F)c1] |

TABLE I-continued

| Compound number | Structure |
|---|---|
| I-13 | |
| I-15 | |
| I-16 | |
| I-17 | |
| I-18 | |
| I-19 | |
| I-20 | 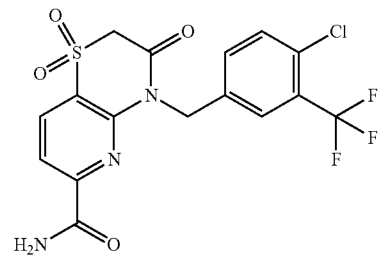 [SMILES: NC(=O)c1ccc2c(n1)N(Cc1ccc(Cl)c(C(F)(F)F)c1)C(=O)CS2(=O)=O] |
| I-21 | 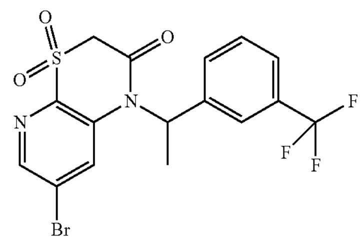 [SMILES: CC(c1cccc(C(F)(F)F)c1)N1C(=O)CS(=O)(=O)c2ncc(Br)cc21] |
| I-22 | 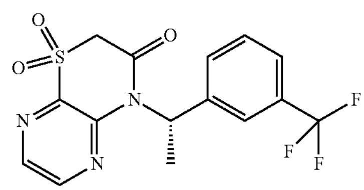 [SMILES: C[C@@H](c1cccc(C(F)(F)F)c1)N1C(=O)CS(=O)(=O)c2nccnc21] |
| I-23 | 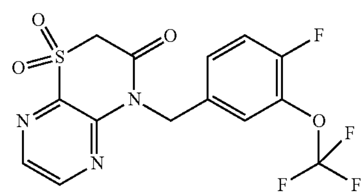 [SMILES: O=C1CS(=O)(=O)c2nccnc2N1Cc1ccc(F)c(OC(F)(F)F)c1] |
| I-24 | 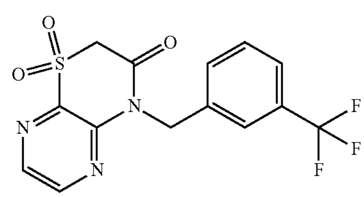 [SMILES: O=C1CS(=O)(=O)c2nccnc2N1Cc1cccc(C(F)(F)F)c1] |
| I-25 | 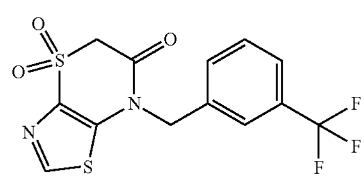 [SMILES: O=C1CS(=O)(=O)c2ncsc2N1Cc1cccc(C(F)(F)F)c1] |
| I-26 | 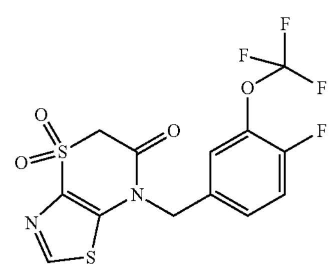 [SMILES: O=C1CS(=O)(=O)c2ncsc2N1Cc1ccc(F)c(OC(F)(F)F)c1] |

TABLE I-continued

| Compound number | Structure |
|---|---|
| I-27 | (structure) |
| I-28 | (structure) |
| I-29 | (structure) |
| I-30 | (structure) |
| I-31 | (structure) |
| I-32 | (structure) |
| I-33 | (structure) |
| I-34 | (structure) |
| I-35 | (structure) |
| I-36 | (structure) |
| I-37 | (structure) |
| I-38 | (structure) |

TABLE I-continued

| Compound number | Structure |
|---|---|
| I-39 | 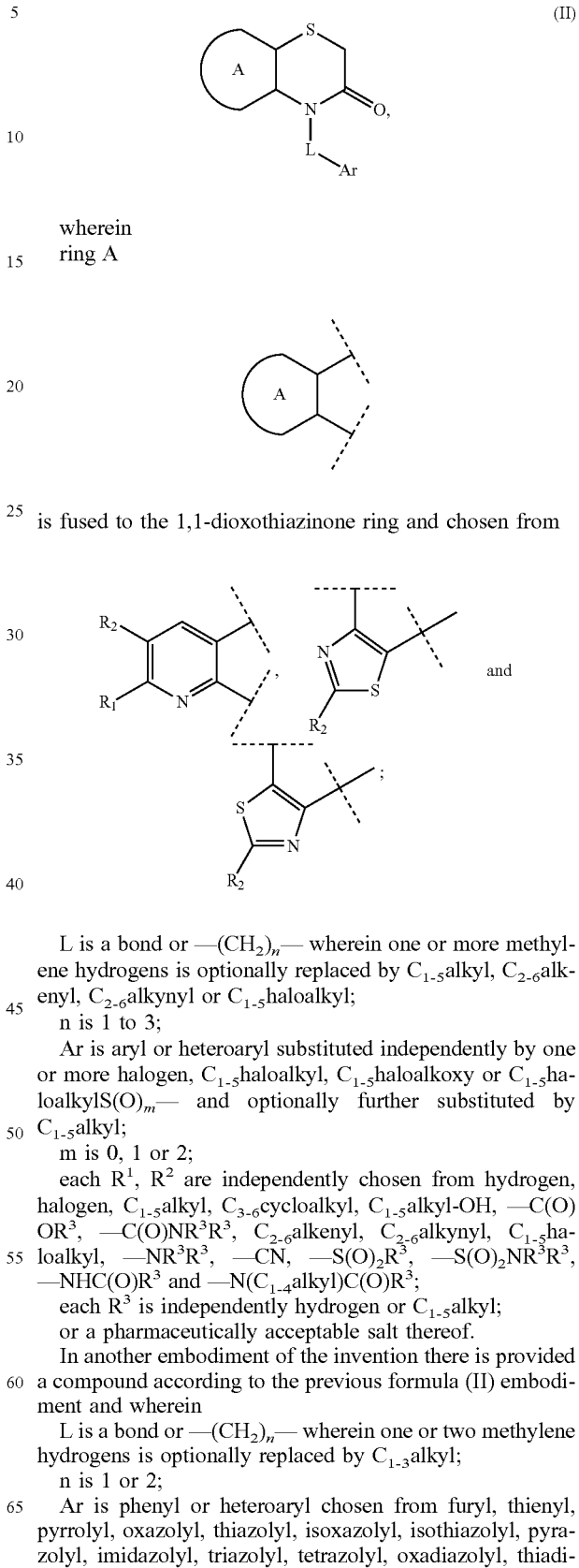 |
| I-40 | 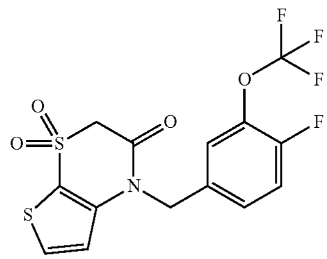 [SMILES: O=C1CS(=O)(=O)c2sccc2N1Cc1ccc(F)c(OC(F)(F)F)c1] |
| I-41 | 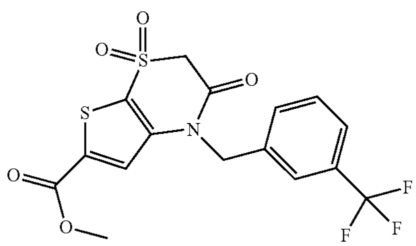 [SMILES: COC(=O)c1cc2c(s1)S(=O)(=O)CC(=O)N2Cc1cccc(C(F)(F)F)c1] |
| I-42 | 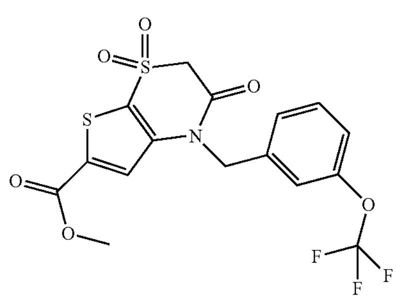 [SMILES: COC(=O)c1cc2c(s1)S(=O)(=O)CC(=O)N2Cc1cccc(OC(F)(F)F)c1] |
| I-43 | 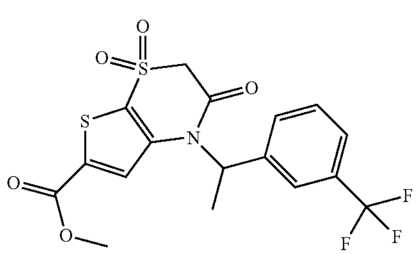 [SMILES: COC(=O)c1cc2c(s1)S(=O)(=O)CC(=O)N2C(C)c1cccc(C(F)(F)F)c1] |

Another aspect of the invention relates to compounds of formula (II)

$$\text{(II)}$$

wherein
ring A is fused to the 1,1-dioxothiazinone ring and chosen from and

L is a bond or —(CH$_2$)$_n$— wherein one or more methylene hydrogens is optionally replaced by C$_{1-5}$alkyl, C$_{2-6}$alkenyl, C$_{2-6}$alkynyl or C$_{1-5}$haloalkyl;
n is 1 to 3;
Ar is aryl or heteroaryl substituted independently by one or more halogen, C$_{1-5}$haloalkyl, C$_{1-5}$haloalkoxy or C$_{1-5}$haloalkylS(O)$_m$— and optionally further substituted by C$_{1-5}$alkyl;
m is 0, 1 or 2;
each R$^1$, R$^2$ are independently chosen from hydrogen, halogen, C$_{1-5}$alkyl, C$_{3-6}$cycloalkyl, C$_{1-5}$alkyl-OH, —C(O)OR$^3$, —C(O)NR$^3$R$^3$, C$_{2-6}$alkenyl, C$_{2-6}$alkynyl, C$_{1-5}$haloalkyl, —NR$^3$R$^3$, —CN, —S(O)$_2$R$^3$, —S(O)$_2$NR$^3$R$^3$, —NHC(O)R$^3$ and —N(C$_{1-4}$alkyl)C(O)R$^3$;
each R$^3$ is independently hydrogen or C$_{1-5}$alkyl;
or a pharmaceutically acceptable salt thereof.

In another embodiment of the invention there is provided a compound according to the previous formula (II) embodiment and wherein
L is a bond or —(CH$_2$)$_n$— wherein one or two methylene hydrogens is optionally replaced by C$_{1-3}$alkyl;
n is 1 or 2;
Ar is phenyl or heteroaryl chosen from furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl, each Ar is substituted independently by one or more halogen, $C_{1-5}$haloalkyl, $C_{1-6}$haloalkoxy or $C_{1-5}$haloalkylS(O)$_m$— and Ar is optionally further substituted by $C_{1-3}$alkyl;
m is 0 or 2;
each $R^1$, $R^2$ are independently chosen from hydrogen, halogen, $C_{1-3}$alkyl, $C_{3-5}$cycloalkyl, $C_{1-3}$alkyl-OH, and —C(O)NR$^3$R$^3$;
each $R^3$ is independently hydrogen or $C_{1-3}$ alkyl;
or a pharmaceutically acceptable salt thereof.

In another embodiment of the invention there is provided a compound according to the any of the formula (II) embodiments hereinabove and wherein
L is a bond or —(CH$_2$)$_n$— wherein one methylene hydrogen is optionally replaced by methyl;
n is 1 or 2;
Ar is phenyl or heteroaryl chosen from pyrazolyl and pyridyl, each Ar is substituted independently by one or more halogen, $C_{1-3}$haloalkyl, $C_{1-3}$haloalkoxy or $C_{1-3}$haloalkylS(O)$_m$— and Ar is optionally further substituted by $C_{1-3}$alkyl;
m is 0 or 2;
each $R^1$, $R^2$ are independently chosen from hydrogen, halogen, $C_{1-3}$alkyl, $C_{3-5}$cycloalkyl, $C_{1-3}$alkyl-OH and —C(O)NR$^3$R$^3$;
each $R^3$ is independently hydrogen or $C_{1-3}$alkyl;
or a pharmaceutically acceptable salt thereof.

In another embodiment of the invention there is provided a compound according to the any of the formula (II) embodiments hereinabove and wherein
Ar is phenyl or pyrazolyl, each Ar is substituted independently by one or more Cl, F, Br, CF$_3$, —OCF$_3$ or —S(O)$_2$—CF$_3$ and Ar is optionally further substituted by methyl;
each $R^1$, $R^2$ are independently chosen from hydrogen, halogen, $C_{1-3}$alkyl, $C_{3-5}$cycloalkyl, $C_{1-3}$alkyl-OH and —C(O)NR$^3$R$^3$;
each $R^3$ is independently hydrogen or methyl;
or a pharmaceutically acceptable salt thereof.

In another embodiment of the invention there is provided a compound according to the any of the formula (II) embodiments hereinabove and wherein
ring A

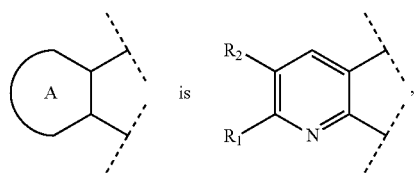

$R^1$ is hydrogen, $C_{1-3}$alkyl-OH, $C_{1-3}$alkyl, $C_{3-5}$cycloalkyl or —C(O)—NH$_2$;
$R^2$ is hydrogen or Cl;
or a pharmaceutically acceptable salt thereof.

In another embodiment of the invention there is provided a compound according to the any of the formula (II) embodiments hereinabove and wherein
ring A

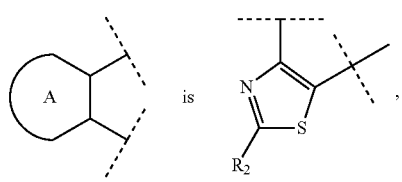

$R_2$ is hydrogen, methyl or cyclopropyl.
or a pharmaceutically acceptable salt thereof.

In another embodiment of the invention there is provided a compound according to the any of the formula (II) embodiments hereinabove and wherein
ring A

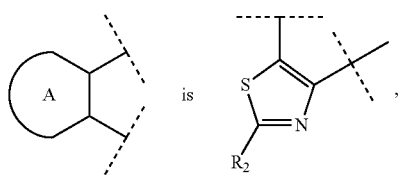

$R_2$ is methyl or isopropyl;
or a pharmaceutically acceptable salt thereof.

In another embodiment of the invention there is provided a compound according to the any of the formula (II) embodiments hereinabove and wherein the combination of L-Ar is

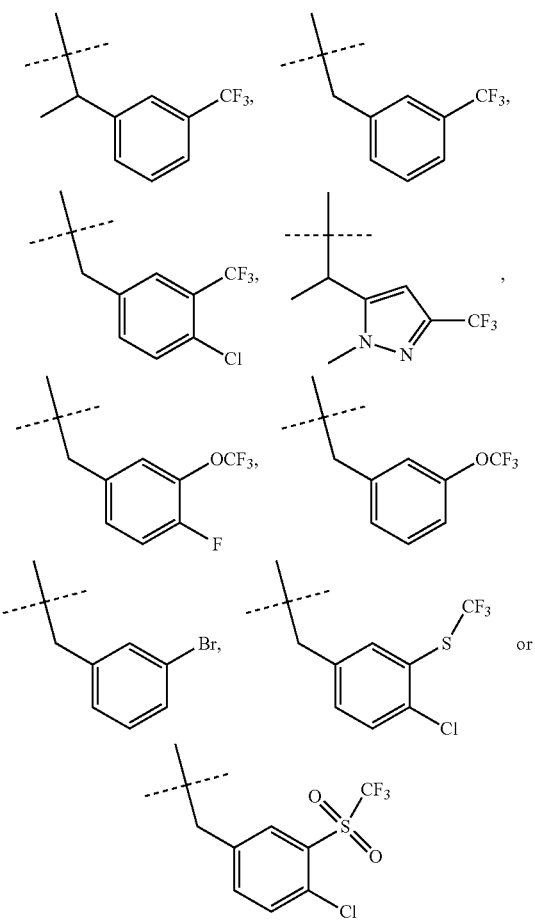

or a pharmaceutically acceptable salt thereof.

In another embodiment, the invention provides the following compounds in Table II which can be made in view of the general schemes, examples and methods known in the art.

TABLE II
| Compound number | Structure |
|---|---|
| II-1 | 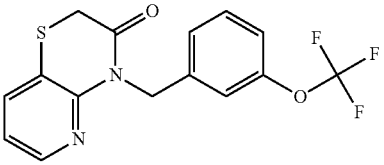 [SMILES: O=C1CSc2cccnc2N1Cc1cccc(OC(F)(F)F)c1] |
| II-2 | 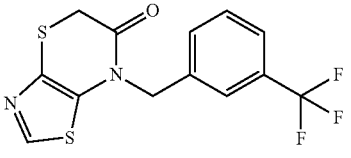 |
| II-3 | 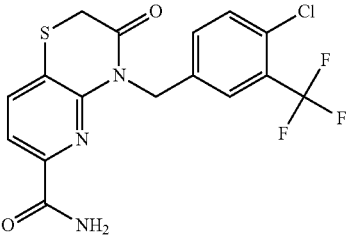 [SMILES: NC(=O)c1ccc2c(n1)N(Cc1ccc(Cl)c(C(F)(F)F)c1)C(=O)CS2] |
| II-4 | 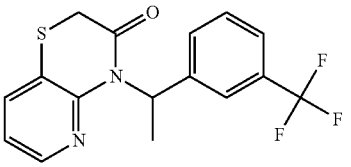 [SMILES: CC(c1cccc(C(F)(F)F)c1)N1C(=O)CSc2cccnc21] |
| II-5 | 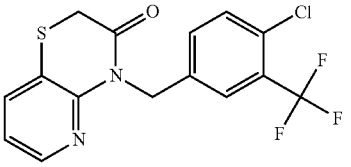 [SMILES: O=C1CSc2cccnc2N1Cc1ccc(Cl)c(C(F)(F)F)c1] |
| II-6 | 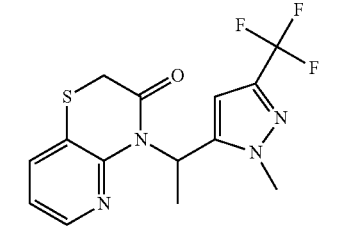 [SMILES: CC(c1cc(C(F)(F)F)nn1C)N1C(=O)CSc2cccnc21] |
| II-7 | 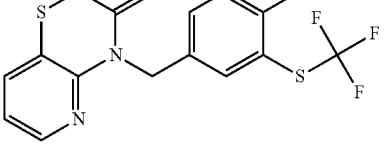 |
| II-8 | 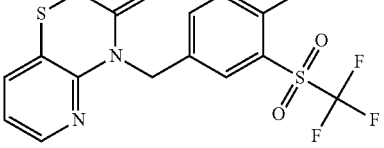 |
| II-9 | 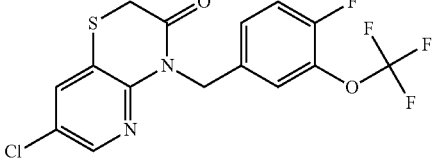 |
| II-10 | 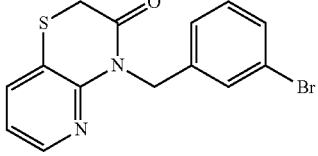 |
| II-11 | 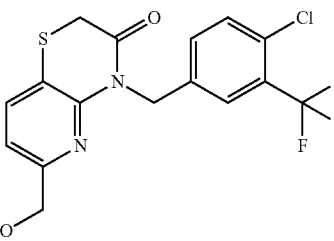 |
| II-12 | 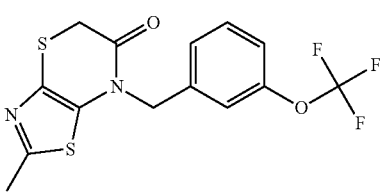 [SMILES: Cc1nc2c(s1)N(Cc1cccc(OC(F)(F)F)c1)C(=O)CS2] |
| II-13 | 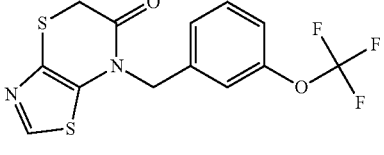 |
| II-14 | 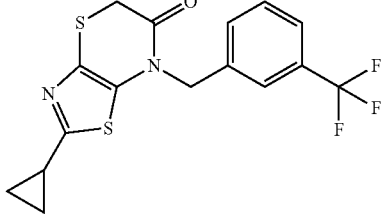 |
| II-15 | 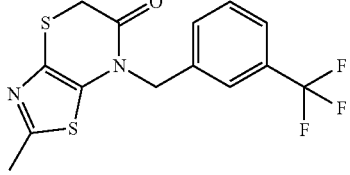 |
| II-16 | 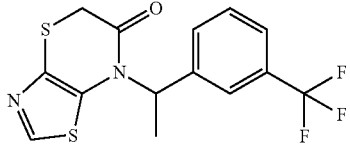 |

TABLE II-continued

| Compound number | Structure |
|---|---|
| II-17 | 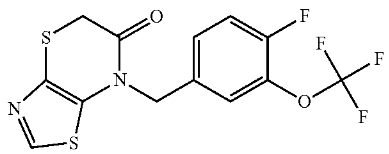 [SMILES: O=C1CSc2ncsc2N1Cc1ccc(F)c(OC(F)(F)F)c1] |
| II-18 | 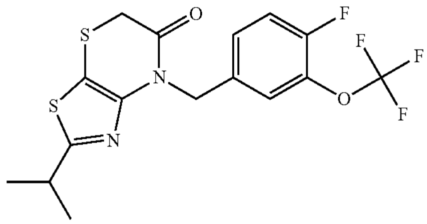 [SMILES: CC(C)c1nc2c(s1)SCC(=O)N2Cc1ccc(F)c(OC(F)(F)F)c1] |
| II-19 | 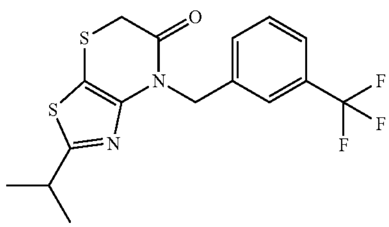 [SMILES: CC(C)c1nc2c(s1)SCC(=O)N2Cc1cccc(C(F)(F)F)c1] |
| II-20 | 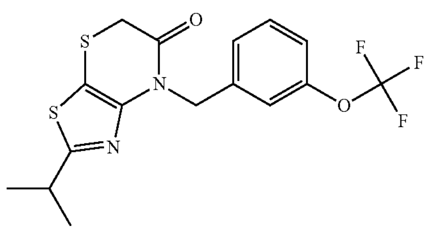 [SMILES: CC(C)c1nc2c(s1)SCC(=O)N2Cc1cccc(OC(F)(F)F)c1] |
| II-21 | 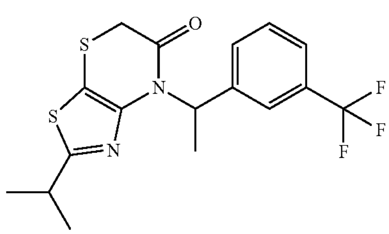 [SMILES: CC(C)c1nc2c(s1)SCC(=O)N2C(C)c1cccc(C(F)(F)F)c1] |
| II-22 | 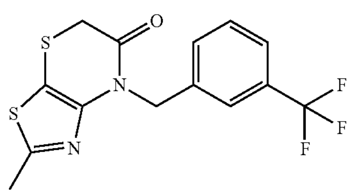 [SMILES: Cc1nc2c(s1)SCC(=O)N2Cc1cccc(C(F)(F)F)c1] |
| II-23 | 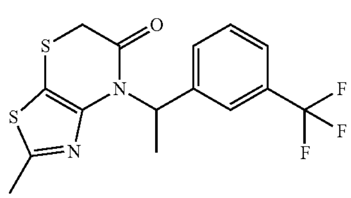 [SMILES: Cc1nc2c(s1)SCC(=O)N2C(C)c1cccc(C(F)(F)F)c1] |

The present invention further relates to metabolites, and prodrugs of compounds of the formulas (I) & (II).

The present invention further relates to a pharmaceutically acceptable salt of a compound of the formula (I) & (II) with an organic or organic acids or bases.

In another aspect the invention relates to compounds of formula (I) & (II)—or the pharmaceutically acceptable salts thereof—as medicaments.

In another aspect the invention relates to compounds of formula (I) & (II)—or the pharmaceutically acceptable salts thereof—for use in a method for treatment of a patient.

In another aspect the invention relates to compounds of formula (I) & (II)—or the pharmaceutically acceptable salts thereof—for use in the treatment of inflammations and autoimmune diseases.

In another aspect the invention relates to the use of compounds of formula (I) & (II)—or the pharmaceutically acceptable salts thereof—for preparing a pharmaceutical composition for the treatment inflammations and autoimmune diseases.

In another aspect the invention relates to a method for the treatment of inflammatory, autoimmune, oncological diseases, cardiovacular or metabolic disorders comprising administering a therapeutically effective amount of a compound of formula (I) & (II)—or one of the pharmaceutically acceptable salts thereof—to a patient.

In another aspect the invention relates to a pharmaceutical preparation containing as active substance one or more compounds of formula (I) & (II)—or the pharmaceutically acceptable salts thereof—optionally in combination with conventional excipients and/or carriers.

Definitions

Terms that are not specifically defined here have the meanings that are apparent to the skilled man in the light of the overall disclosure and the context as a whole.

As used herein, the following definitions apply, unless stated otherwise:

The use of the prefix $C_{x-y}$, wherein x and y each represent a natural number, indicates that the chain or ring structure or combination of chain and ring structure as a whole, specified and mentioned in direct association, may consist of a maximum of y and a minimum of x carbon atoms.

Alkyl denotes monovalent, saturated hydrocarbon chains, which may be present in both straight-chain (unbranched) and branched form. If an alkyl is substituted, the substitution may take place independently of one another, by mono- or polysubstitution in each case, on all the hydrogen-carrying carbon atoms.

For example, the term "$C_{1-5}$alkyl" includes for example $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

Further examples of alkyl are methyl (Me; —$CH_3$), ethyl (Et; —$CH_2CH_3$), 1-propyl (n-propyl; n-Pr; —$CH_2CH_2CH_3$), 2-propyl (i-Pr; iso-propyl; —$CH(CH_3)_2$), 1-butyl (n-butyl; n-Bu; —$CH_2CH_2CH_2CH_3$), 2-methyl-1-propyl (iso-butyl; i-Bu; —$CH_2CH(CH_3)_2$), 2-butyl (sec-butyl; sec-Bu; —$CH(CH_3)CH_2CH_3$), 2-methyl-2-propyl (tert-butyl; t-Bu; —$C(CH_3)_3$), 1-pentyl (n-pentyl; —$CH_2CH_2CH_2CH_2CH_3$), 2-pentyl (—$CH(CH_3)$ $CH_2CH_2CH_3$), 3-pentyl (—$CH(CH_2CH_3)_2$), 3-methyl-1-butyl (iso-pentyl; —$CH_2CH_2CH(CH_3)_2$), 2-methyl-2-butyl (—$C(CH_3)_2CH_2CH_3$), 3-methyl-2-butyl (—$CH(CH_3)CH$ (CH₃)₂), 2,2-dimethyl-1-propyl (neo-pentyl; —CH₂C(CH₃)₃), 2-methyl-1-butyl (—CH₂CH(CH₃)CH₂CH₃), 1-hexyl (n-hexyl; —CH₂CH₂CH₂CH₂CH₂CH₃), 2-hexyl (—CH(CH₃)CH₂CH₂CH₂CH₃), 3-hexyl (—CH(CH₃)(CH₂CH₂CH₃)), 2-methyl-2-pentyl (—C(CH₃)₂CH₂CH₂CH₃), 3-methyl-2-pentyl (—CH(CH₃)CH(CH₃)CH₂CH₃), 4-methyl-2-pentyl (—CH(CH₃)CH₂CH(CH₃)₂), 3-methyl-3-pentyl (—C(CH₃)(CH₂CH₃)₂), 2-methyl-3-pentyl (—CH(CH₂CH₃)CH(CH₃)₂), 2,3-dimethyl-2-butyl (—C(CH₃)₂CH(CH₃)₂), 3,3-dimethyl-2-butyl (—CH(CH₃)C(CH₃)₃), 2,3-dimethyl-1-butyl (—CH₂CH(CH₃)CH(CH₃)CH₃), 2,2-dimethyl-1-butyl (—CH₂C(CH₃)₂CH₂CH₃), 3,3-dimethyl-1-butyl (—CH₂CH₂C(CH₃)₃), 2-methyl-1-pentyl (—CH₂CH(CH₃)CH₂CH₂CH₃), 3-methyl-1-pentyl (—CH₂CH₂CH(CH₃)CH₂CH₃), 1-heptyl (n-heptyl), 2-methyl-1-hexyl, 3-methyl-1-hexyl, 2,2-dimethyl-1-pentyl, 2,3-dimethyl-1-pentyl, 2,4-dimethyl-1-pentyl, 3,3-dimethyl-1-pentyl, 2,2,3-trimethyl-1-butyl, 3-ethyl-1-pentyl, 1-octyl (n-octyl), 1-nonyl (n-nonyl); 1-decyl (n-decyl) etc.

By the terms propyl, butyl, pentyl, hexyl, heptyl, octyl, nonyl, decyl etc. without any further definition are meant saturated hydrocarbon groups with the corresponding number of carbon atoms, wherein all isomeric forms are included.

The above definition for alkyl also applies if alkyl is a part of another (combined) group such as for example $C_{x-y}$alkylamino or $C_{x-y}$alkoxy.

Unlike alkyl, alkenyl consists of at least two carbon atoms, wherein at least two adjacent carbon atoms are joined together by a C—C double bond and a carbon atom can only be part of one C—C double bond. If in an alkyl as hereinbefore defined having at least two carbon atoms, two hydrogen atoms on adjacent carbon atoms are formally removed and the free valencies are saturated to form a second bond, the corresponding alkenyl is formed.

Examples of alkenyl are vinyl (ethenyl), prop-1-enyl, allyl (prop-2-enyl), isopropenyl, but-1-enyl, but-2-enyl, but-3-enyl, 2-methyl-prop-2-enyl, 2-methyl-prop-1-enyl, 1-methyl-prop-2-enyl, 1-methyl-prop-1-enyl, 1-methylidenepropyl, pent-1-enyl, pent-2-enyl, pent-3-enyl, pent-4-enyl, 3-methyl-but-3-enyl, 3-methyl-but-2-enyl, 3-methyl-but-1-enyl, hex-1-enyl, hex-2-enyl, hex-3-enyl, hex-4-enyl, hex-5-enyl, 2,3-dimethyl-but-3-enyl, 2,3-dimethyl-but-2-enyl, 2-methylidene-3-methylbutyl, 2,3-dimethyl-but-1-enyl, hexa-1,3-dienyl, hexa-1,4-dienyl, penta-1,4-dienyl, penta-1,3-dienyl, buta-1,3-dienyl, 2,3-dimethylbuta-1,3-diene etc.

By the generic terms propenyl, butenyl, pentenyl, hexenyl, butadienyl, pentadienyl, hexadienyl, heptadienyl, octadienyl, nonadienyl, decadienyl etc. without any further definition are meant all the conceivable isomeric forms with the corresponding number of carbon atoms, i.e. propenyl includes prop-1-enyl and prop-2-enyl, butenyl includes but-1-enyl, but-2-enyl, but-3-enyl, 1-methyl-prop-1-enyl, 1-methyl-prop-2-enyl etc.

Alkenyl may optionally be present in the cis or trans or E or Z orientation with regard to the double bond(s).

The above definition for alkenyl also applies when alkenyl is part of another (combined) group such as for example in $C_{x-y}$alkenylamino or $C_{x-y}$alkenyloxy.

Unlike alkyl, alkynyl consists of at least two carbon atoms, wherein at least two adjacent carbon atoms are joined together by a C—C triple bond. If in an alkyl as hereinbefore defined having at least two carbon atoms, two hydrogen atoms in each case at adjacent carbon atoms are formally removed and the free valencies are saturated to form two further bonds, the corresponding alkynyl is formed.

Examples of alkynyl are ethynyl, prop-1-ynyl, prop-2-ynyl, but-1-ynyl, but-2-ynyl, but-3-ynyl, 1-methyl-prop-2-ynyl, pent-1-ynyl, pent-2-ynyl, pent-3-ynyl, pent-4-ynyl, 3-methyl-but-1-ynyl, hex-1-ynyl, hex-2-ynyl, hex-3-ynyl, hex-4-ynyl, hex-5-ynyl etc.

By the generic terms propynyl, butynyl, pentynyl, hexynyl, heptynyl, octynyl, nonynyl, decynyl etc. without any further definition are meant all the conceivable isomeric forms with the corresponding number of carbon atoms, i.e. propynyl includes prop-1-ynyl and prop-2-ynyl, butynyl includes but-1-ynyl, but-2-ynyl, but-3-ynyl, 1-methyl-prop-1-ynyl, 1-methyl-prop-2-ynyl, etc.

If a hydrocarbon chain carries both at least one double bond and also at least one triple bond, by definition it belongs to the alkynyl subgroup.

The above definition for alkynyl also applies if alkynyl is part of another (combined) group, as for example in $C_{x-y}$alkynylamino or $C_{x-y}$alkynyloxy.

Haloalkyl (haloalkenyl, haloalkynyl) is derived from the previously defined alkyl (alkenyl, alkynyl) by replacing one or more hydrogen atoms of the hydrocarbon chain independently of one another by halogen atoms, which may be identical or different. If a haloalkyl (haloalkenyl, haloalkynyl) is to be further substituted, the substitutions may take place independently of one another, in the form of mono- or polysubstitutions in each case, on all the hydrogen-carrying carbon atoms.

Examples of haloalkyl (haloalkenyl, haloalkynyl) are —CF₃, —CHF₂, —CH₂F, —CF₂CF₃, —CHFCF₃, —CH₂CF₃, —CF₂CH₃, —CHFCH₃, —CF₂CF₂CF₃, —CF₂CH₂CH₃, —CF=CF₂, —CCl=CH₂, —CBr=CH₂, —CC≡CF₃, —CHFCH₂CH₃, —CHFCH₂CF₃ etc.

From the previously defined haloalkyl (haloalkenyl, haloalkynyl) are also derived the terms haloalkylene (haloalkenylene, haloalkynylene). Haloalkylene (haloalkenylene, haloalkynylene), unlike haloalkyl (haloalkenyl, haloalkynyl), is bivalent and requires two binding partners. Formally, the second valency is formed by removing a hydrogen atom from a haloalkyl (haloalkenyl, haloalkynyl).

Corresponding groups are for example —CH₂F and —CHF—, —CHFCH₂F and —CHFCHF— or >CFCH₂F etc.

The above definitions also apply if the corresponding halogen-containing groups are part of another (combined) group, for example alkoxyhaloalkyl such as —O—CF₃, thiohaloalkyl such as —S—CF₃ and sulphonylhalolalkyl such as —S(O)₂—CF₃.

Halogen relates to fluorine, chlorine, bromine and/or iodine atoms.

Cycloalkyl is made up of the subgroups monocyclic hydrocarbon rings, bicyclic hydrocarbon rings and spirohydrocarbon rings. The systems are saturated. In bicyclic hydrocarbon rings two rings are joined together so that they have at least two carbon atoms together. In spiro-hydrocarbon rings one carbon atom (spiroatom) belongs to two rings together.

If a cycloalkyl is to be substituted, the substitutions may take place independently of one another, in the form of mono- or polysubstitutions in each case, on all the hydrogen-carrying carbon atoms. Cycloalkyl itself may be linked as a substituent to the molecule via every suitable position of the ring system.

Examples of cycloalkyl are cyclopropyl, cyclobutyl, cyclopentyl, cyclohexyl, cycloheptyl. Corresponding groups are an example:

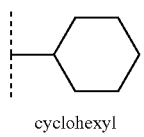
cyclohexyl

Aryl denotes mono-, bi- or tricyclic carbocycles with at least one aromatic carbocycle. Preferably, it denotes a monocyclic group with six carbon atoms (phenyl) or a bicyclic group with nine or ten carbon atoms (two six-membered rings or one six-membered ring with a five-membered ring), wherein the second ring may also be aromatic or, however, may also be saturated or partially saturated.

If an aryl is to be substituted, the substitutions may take place independently of one another, in the form of mono- or polysubstitutions in each case, on all the hydrogen-carrying carbon atoms. Aryl itself may be linked as a substituent to the molecule via every suitable position of the ring system.

Examples of aryl are phenyl, naphthyl, indanyl (2,3-dihydroindenyl), indenyl, anthracenyl, phenanthrenyl, tetrahydronaphthyl (1,2,3,4-tetrahydronaphthyl, tetralinyl), dihydronaphthyl (1,2-dihydronaphthyl), fluorenyl etc.

The above definition of aryl also applies if aryl is part of another (combined) group as for example in arylamino, aryloxy or arylalkyl.

Heterocyclyl denotes ring systems, which are derived from the previously defined cycloalkyl by replacing one or more of the groups —CH$_2$— independently of one another in the hydrocarbon rings by the groups —O—, —S— or —NH—, wherein a total of not more than five heteroatoms may be present, at least one carbon atom may be present between two oxygen atoms and between two sulphur atoms or between one oxygen and one sulphur atom and the ring as a whole must have chemical stability. Heteroatoms may optionally be present in all the possible oxidation stages (sulphur→sulphoxide —SO—, sulphone —SO$_2$—; nitrogen→N-oxide).

If a heterocyclyl is substituted, the substitutions may take place independently of one another, in the form of mono- or polysubstitutions in each case, on all the hydrogen-carrying carbon and/or nitrogen atoms. Heterocyclyl itself may be linked as a substituent to the molecule via every suitable position of the ring system.

Examples of heterocyclyl are tetrahydrofuryl, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S, S-dioxide, 1,3-dioxolanyl, tetrahydropyranyl, tetrahydrothiopyranyl.

Heteroaryl denotes monocyclic heteroaromatic rings or polycyclic rings with at least one heteroaromatic ring, which compared with the corresponding aryl or cycloalkyl, instead of one or more carbon atoms, one or more identical or different heteroatoms, selected independently of one another from among nitrogen, sulphur and oxygen, wherein the resulting group must be chemically stable. The prerequisite for the presence of heteroaryl is a heteroatom and a heteroaromatic system.

If a heteroaryl is to be substituted, the substitutions may take place independently of one another, in the form of mono- or polysubstitutions in each case, on all the hydrogen-carrying carbon and/or nitrogen atoms. Heteroaryl itself may be linked as a substituent to the molecule via every suitable position of the ring system, both carbon and nitrogen.

Examples of heteroaryl are furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl, indolyl, isoindolyl, benzofuryl, benzothienyl, benzoxazolyl, benzothiazolyl, benzisoxazolyl, benzisothiazolyl, benzimidazolyl, indazolyl, isoquinolinyl, quinolinyl, quinoxalinyl, cinnolinyl, phthalazinyl, quinazolinyl, benzotriazinyl, indolizinyl, oxazolopyridyl, imidazopyridyl, naphthyridinyl, benzoxazolyl, pyridopyridyl, pyrimidopyridyl, purinyl, pteridinyl, benzothiazolyl, imidazopyridyl, imidazothiazolyl, and the like.

Heteroatoms may optionally be present in all the possible oxidation stages (sulphur→sulphoxide —SO—, sulphone —SO$_2$—; nitrogen→N-oxide).

All cyclic and acyclic systems defined in this section hereinabove shall be understood to be optionally partially or fully halogenated where possible and unless otherwise indicated.

Stereochemistry/solvates/hydrates: Unless specifically indicated, throughout the specification and appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof. The compounds and salts of the invention can exist in unsolvated as well as solvated forms with pharmaceutically acceptable solvents such as water, ethanol and the like. In general, the solvated forms such as hydrates are considered equivalent to the unsolvated forms for the purposes of the invention.

Salts: The phrase "pharmaceutically acceptable" is employed herein to refer to those compounds, materials, compositions, and/or dosage forms which are, within the scope of sound medical judgement, suitable for use in contact with the tissues of human beings and animals without excessive toxicity, irritation, allergic response, or other problem or complication, and commensurate with a reasonable benefit/risk ratio.

As used herein "pharmaceutically acceptable salts" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include acetates, ascorbates, benzenesulphonates, benzoates, besylates, bicarbonates, bitartrates, bromides/hydrobromides, Ca-edetates/edetates, camsylates, carbonates, chlorides/hydrochlorides, citrates, edisylates, ethane disulphonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulphonates, mesylates, methylbromides, methylnitrates, methylsulphates, mucates, napsylates, nitrates, oxalates, pamoates, pantothenates, phenyl acetates, phosphates/diphosphates, polygalacturonates, propionates, salicylates, stearates, subacetates, succinates, sulphamides, sulphates, tannates, tartrates, teoclates, toluenesulphonates, triethiodides, ammonium, benzathines, chloroprocaines, cholines, diethanolamines, ethylenediamines, meglumines and procaines.

Further pharmaceutically acceptable salts can be formed with cations from metals like aluminium, calcium, lithium, magnesium, potassium, sodium, zinc and the like (also see Pharmaceutical salts, Birge, S. M. et al., J. Pharm. Sci., (1977), 66, 1-19).

The pharmaceutically acceptable salts of the present invention can be synthesised from the to parent compound which contains a basic or acidic moiety by conventional chemical methods. Generally, such salts can be prepared by reacting the free acid or base form of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoroacetates), also comprise a part of the invention.

Some abbreviated notations and their structure correspondences are listed below: In a representation such as for example

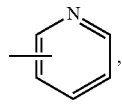

the solid line means that the ring system may be attached to the molecule via the carbon atom 1, 2 or 3, and is thus equivalent to the following representation

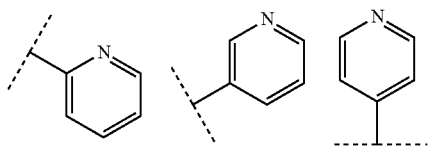

By a therapeutically effective amount for the purposes of this invention is meant a quantity of substance that is capable of obviating symptoms of illness or alleviating these symptoms, or which prolong the survival of a treated patient.

List of abbreviations

| | |
|---|---|
| Ac | Acetyl |
| ACN | Acetonitrile |
| aq. | aquatic, aqueous |
| ATP | adenosine triphosphate |
| BiPh | Biphenyl |
| Bn | Benzyl |
| Boc | tert-butyloxycarbonyl |
| Bu | Butyl |
| c | Concentration |
| d | day(s) |
| dba | Dibenzylideneacetone |
| TLC | thin layer chromatography |
| Davephos | 2-dimethylamino-2'-dicyclohexylaminophosphinobiphenyl |
| DBA | Dibenzylideneacetone' |
| DCM | Dichloromethane |
| DEA | Diethylamine |
| DMAP | 4-N,N-dimethylaminopyridine |
| DME | 1,2-dimethoxyethane |
| DMF | N,N-dimethylformamide |
| DMSO | Dimethylsulphoxide |
| DPPA | Diphenylphosphorylazide |

List of abbreviations-continued

| | |
|---|---|
| dppf | 1.1'-bis(diphenylphosphino)ferrocene |
| EDTA | ethylenediaminetetraacetic acid |
| EGTA | ethyleneglycoltetraacetic acid |
| equiv. | equivalent(s) |
| ESI | electron spray ionization |
| Et | Ethyl |
| Et$_2$O | diethyl ether |
| EtOAc | ethyl acetate |
| EtOH | Ethanol |
| h | Hour |
| HATU | O-(7-azabenzotriazol-1-yl)-N,N,N',N'-tetramethyl-uronium hexafluorophosphate |
| hept | Heptane |
| HPLC | high performance liquid chromatography |
| i | Iso |
| Kat., kat. | catalyst, catalytic |
| conc. | Concentrated |
| LC | liquid chromatography |
| LiHMDS | lithium bis(trimethylsilyl)amide |
| sln. | Solution |
| mCPBA | 3-Chloroperoxbenzoic acid |
| Me | Methyl |
| MeOH | Methanol |
| min | Minutes |
| MPLC | medium pressure liquid chromatography |
| MS | mass spectrometry |
| NBS | N-bromo-succinimide |
| NIS | N-iodo-succinimide |
| NMM | N-methylmorpholine |
| NMP | N-methylpyrrolidone |
| NP | normal phase |
| n.a. | not available |
| PBS | phosphate-buffered saline |
| Ph | Phenyl |
| Pr | Propyl |
| Py | Pyridine |
| rac | Racemic |
| red. | Reduction |
| Rf (R$_f$) | retention factor |
| RP | reversed phase |
| Rt | Retention time (HPLC) |
| rt | ambient temperature |
| S$_N$ | nucleophilic substitution |
| TBAF | tetrabutylammonium fluoride |
| TBDMS | tert-butyldimethylsilyl |
| TBME | tert-butylmethylether |
| TBTU | O-(benzotriazol-l-yl)-N,N,N',N'-tetramethyl-uronium tetrafluoroborate |
| tBu | tert-butyl |
| TEA | Triethylamine |
| temp. | Temperature |
| tert | Tertiary |
| Tf | Triflate |
| TFA | trifluoroacetic acid |
| THF | Tetrahydrofuran |
| TMS | Trimethylsilyl |
| TRIS | tris(hydroxymethyl)-aminomethane |
| TsOH | p-toluenesulphonic acid |
| UV | Ultraviolet |

Features and advantages of the present invention will become apparent from the following detailed examples which illustrate the fundamentals of the invention by way of example without restricting its scope:

PREPARATION OF THE COMPOUNDS ACCORDING TO THE INVENTION

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

The compounds according to the invention are named in accordance with CAS rules using the software Autonom.

HPLC Methods: Analytical LC/MS Analysis Method 1:

Scheme 1: General synthetic routes towards compounds (I and II)

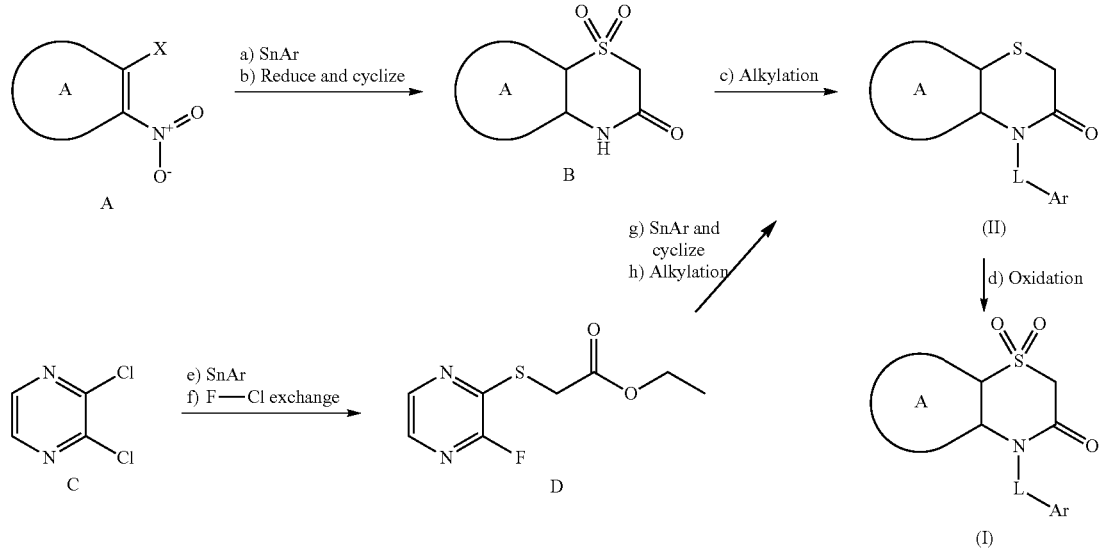

Column: Waters BEH 2.1×50 mm C18 1.7 um column
Gradient:

| Time (min) | 95% Water/5% ACN (0.05% TFA) | ACN (0.05% TFA) | Flow (ml/min) |
|---|---|---|---|
| 0 | 90 | 10 | 0.8 |
| 1.19 | 0 | 100 | 0.8 |
| 1.7 | 0 | 100 | 0.8 |

Analytical LC/MS Analysis Method 2:
Column: Waters BEH 2.1×50 mm C18 1.7 um column
Gradient:

| Time (min) | 95% Water/5% ACN (0.05% TFA) | ACN (0.05% TFA) | Flow (ml/min) |
|---|---|---|---|
| 0 | 90 | 10 | 0.8 |
| 4.5 | 0 | 100 | 0.8 |
| 4.58 | 0 | 100 | 0.8 |

Preparatory HPLC Purification Method:
Column: Waters Sunfire™ Prep OBD™ 5 μm 30×150 mm
Solvents: ACN+0.1% TFA; water+0.1% TFA
Gradient: 0-2 min initial % ACN; 2-18 min gradient to final % ACN; 2 min hold final % ACN.
Peak Collection: UV nM The compounds according to the invention are prepared by the methods of synthesis described hereinafter in which the substituents of the general formulae have the meanings given hereinbefore. These methods are intended as an illustration of the invention without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Compounds (I) according to the invention can be prepared in several ways. One way, as described in the general reaction scheme 1, starts from starting a halogenated nitro-heterocromatic intermediate (A) which are either commercially available or can be synthesized as described below. Through a 3-step procedure, compound (II) can be synthesized. Oxidation of compound II provides compound I. The pyrazino[2,3-b][1,4]thiazin-3-one compounds I and II require a different 4-5-step route using 2,3-dichloropyrazine as the starting material.

Scheme 2

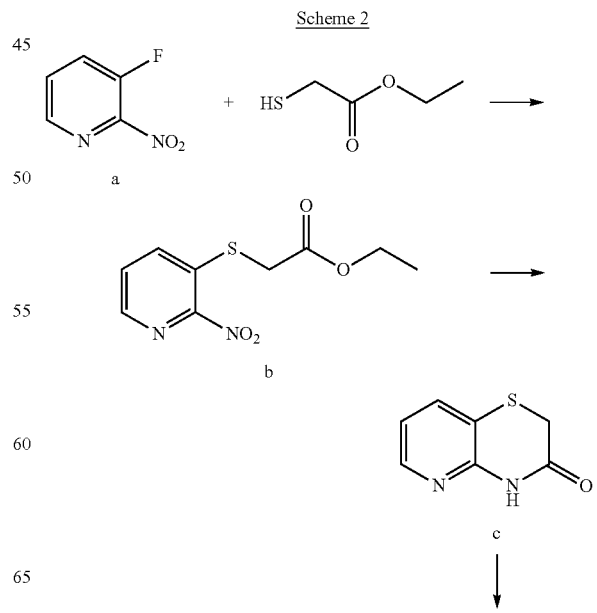

-continued

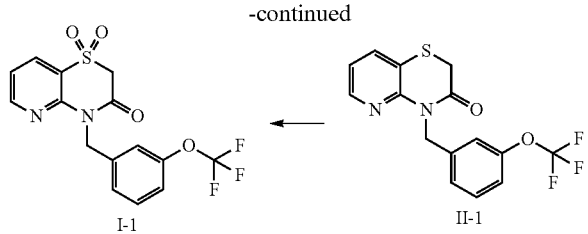

General Procedure 1 for the Preparation of Pyridyl Fused Thiazinones

Preparation of 4-(3-trifluoromethoxy-benzyl)-4H-pyrido[3,2-b][1,4]thiazin-3-one (Compound II-1) and 1,1-dioxo-4-(3-trifluoromethoxy-benzyl)-1,4-dihydro-2H-1lambda*6*-pyrido[3,2-b][1,4]thiazin-3-one (Compound I-1).

Step 1: In a 500 mL flask is placed ethyl thioglycolate (5 g, 41.6 mmol) and 3-fluoro-2-nitropyridine (a, 6.2 g, 43.7 mmol, 1.05 equiv.) in 100 mL of dioxane. This is cooled in an ice bath where to this is added sodium hydride (60% dispersion in mineral oil, 2.0 g, 49.9 mmol, 1.2 equiv.). After 2 h, the reaction is diluted with 200 ml of water and extracted with EtOAc (2×). The organics are rinsed with water×2, brine, dried over $Na_2SO_4$, filtered, and evaporated. The residue is then purified via flash chromatography (0-60% EtOAc/hept). The major peak is combined and evaporated to provide 7.8 g (77%) of the desired (2-nitro-pyridin-3-ylsulfanyl)-acetic acid ethyl ester (b) as a yellow oil.

Step 2: In a 250 mL flask is placed compound b (2.2 g, 9.1 mmol) in 100 mL of glacial AcOH. To this is added iron powder (1.5 g, 27.2 mmol, 3 equiv.) and the reaction is allowed to stir at room temperature for 16 h. The reaction is then heated to 90° C. for 16 h. The reaction is filtered through Celite and the AcOH is removed in vacuo. The residue is then triturated with water and the solids are filtered and dried to provide 1.3 g of compound c which is used without further purification.

Step 3: In a 20 mL vial is placed compound c (100 mg, 0.60 mmol) in 4 mL of DMF. To this is added sodium hydride (60% dispersion, 26 mg, 0.66 mmol, 1.1 equiv.). After gas evolution (3 min) 3-trifluoromethoxybenzyl bromide (184 mg, 0.72 mmol, 1.2 equiv.) is added. After 16 h the reaction is transferred to a sep funnel with water and extracted with EtOAc. The organics were rinsed with brine, dried over $Na_2SO_4$, filtered, and evaporated. The residue is purified via flash chromatography (0-30% EtOAc/hept). The desired fractions are concentrated to provide 163 mg of the desired compound II-1, LC/MS Method 1; Rt=1.57 min.; $[M+H]^+$=341.1.

Step 4: In a 20 mL vial is placed compound II-1 (110 mg, 0.32 mmol) in 10 mL of $CH_2Cl_2$. To this is added mCPBA (77%, 122 mg, 0.71 mmol, 2.2 equiv.) with stirring for 16 h. Crude reaction is then purified with flash chromatography (0-40% EtOAc/hept) to provide 76 mg (63%) of the desired compound I-1. LC/MS Method 1; Rt=1.45 min.; $[M+H]^+$=373.4.

The following compounds are prepared in a similar manner:

TABLE 1

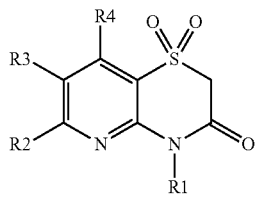

| Compound number | R1 | R2 | R3 | R4 | Rt (min) | HPLC Method # | M+ |
|---|---|---|---|---|---|---|---|
| I-2 | 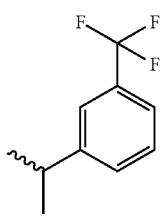 | H | H | H | 0.98 | 1 | 371.1 |
| I-3 | 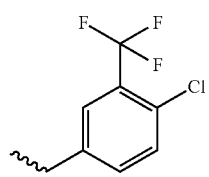 | H | H | H | 1.07 | 1 | 391.1 |

TABLE 1-continued

| Compound number | R1 | R2 | R3 | R4 | Rt (min) | HPLC Method # | M+ |
|---|---|---|---|---|---|---|---|
| I-4 | 2-Cl-5-(CF3)-phenyl-CH(CH3)- | H | H | H | 1.04 | 1 | 405.1 |
| I-5 | 4-F-3-(OCF3)-phenyl-CH(CH3)- | H | H | H | 0.97, 1 | 1 | 390.2 |
| I-6 | 2-(CF3)-phenyl-CH2CH2- | H | H | H | 0.97, 1 | 1 | 371.0 |
| I-7 | 3-(CF3)-phenyl-CH2CH2- | H | H | H | 0.96 | 1 | 371.0 |
| I-8 | 6-(CF3)-pyridin-2-yl-CH(CH3)- | H | H | H | 0.88 | 1 | 373.1 |
| I-9 | 3-(CF3)-phenyl-CH(CH3)- | H | Cl | H | 1.05 | 1 | 404.9 |

TABLE 1-continued
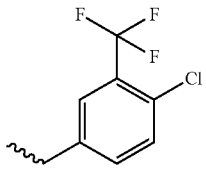
| Compound number | R1 | R2 | R3 | R4 | Rt (min) | HPLC Method # | M+ |
|---|---|---|---|---|---|---|---|
| I-10 | 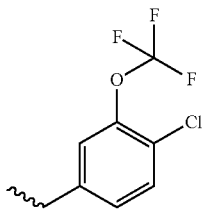 | H | Cl | H | 1.07 | 1 | 424.9 |
| I-12 | 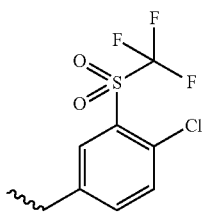 | H | H | H | 1.01 | 1 | 406.9 |
| I-13 | 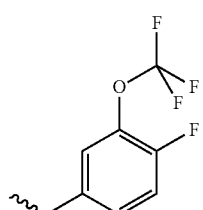 | H | H | H | 0.93 | 1 | 455.0 |
| I-15 | 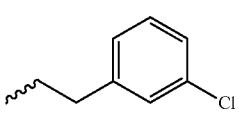 | H | Cl | H | 1.09 | 1 | 424.9 |
| I-16 | 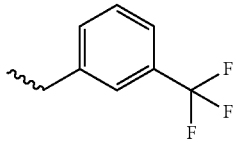 | H | H | H | 0.95 | 1 | 337.4 |
| I-17 | 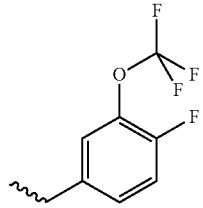 | H | H | H | 0.92 | 1 | 357.4 |
| I-18 |  | O (methyl ester) | H | H | 1.02 | 1 | 449.1 |

TABLE 1-continued
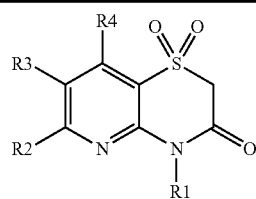
| Compound number | R1 | R2 | R3 | R4 | Rt (min) | HPLC Method # | M+ |
|---|---|---|---|---|---|---|---|
| I-19 | 3-(trifluoromethyl)-α-methylbenzyl | C(O)N(CH3)2 | H | H | 0.92 | 1 | 442.6 |
| I-20 | 4-chloro-3-(trifluoromethyl)-α-methylbenzyl | C(O)NH2 | H | H | 1.05 | 1 | 434.4 |
TABLE 2
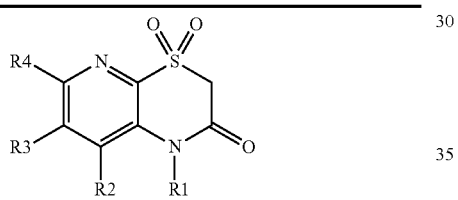
| Compound number | R1 | R2 | R3 | R4 | Rt (min) | HPLC Method | M+ |
|---|---|---|---|---|---|---|---|
| I-21 | 3-(trifluoromethyl)-α-methylbenzyl | H | Br | H | 0.96 | 1 | 450.9 |
Scheme 3
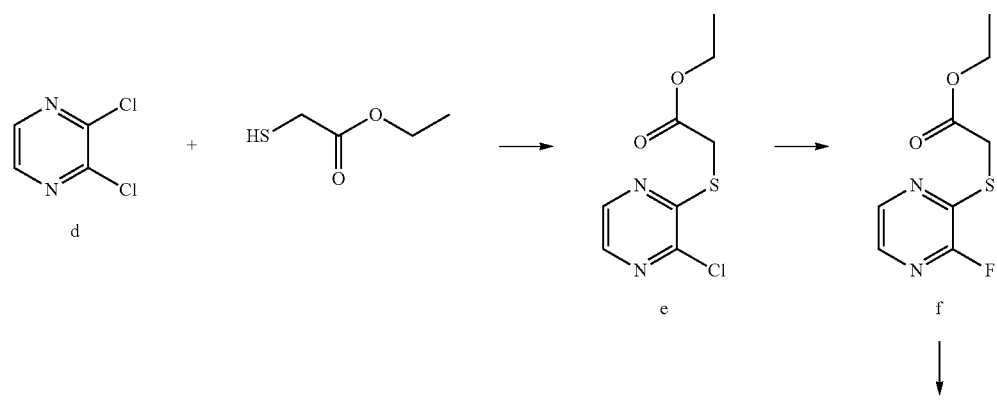

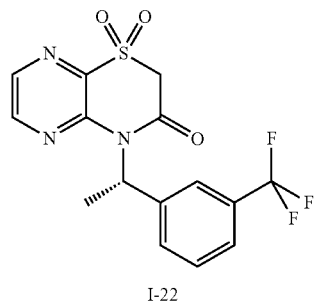 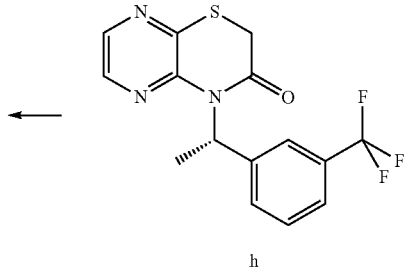 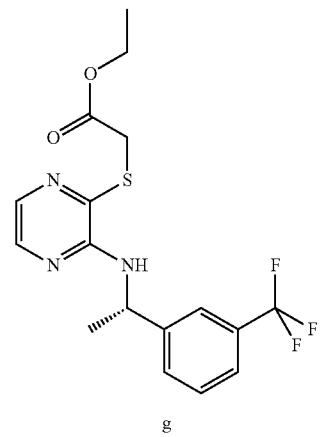

I-22  h  g

General Procedure 2 for the Preparation of Pyrazine Fused Thiazinones

Preparation of 1,1-dioxo-4-[(S)-1-(3-trifluoromethyl-phenyl)-ethyl]-1,4-dihydro-2H-1lambda*6*-pyrazino[2,3-b][1,4]thiazin-3-one (Compound I-22).

Step 1: In a 250 mL flask is placed ethyl thioglycolate (1.0 g, 8.3 mmol, 1 equiv.) and compound d (1.4 g, 9.2 mmol, 1.1 equiv.) in 50 mL of THF. This is cooled to 0° C. where sodium hydride (60% dispersion, 366 mg, 9.2 mmol, 1.1 equiv.) is added. The ice bath is removed after 10 minutes and the reaction is allowed to stir to room temperature for 16 h. The reaction is then diluted with water and extracted with EtOAc. The combined organics are dried over $Na_2SO_4$, filtered and evaporated. The residue is purified via flash chromatography (0-30% EtOAc/hept) to provide 1.33 g (69%) of compound e as a clear oil. This was used without further purification.

Step 2: In a 250 mL flask is placed compound e (2.3 g, 9.9 mmol) and anhydrous potassium fluoride (4.6 g, 79.2 mmol, 8 equiv.) in 80 mL of DMSO. This is then heated at 125° C. for 16 h. Solvents are then removed and the residue is partitioned between $Et_2O$ and water. The organics were dried over $Na_2SO_4$, filtered and evaporated. The residue is purified via flash chromatography (0-30% EtOAc/hept) to provide 482 mg (22%) of compound f which is used without further purification.

Step 3: In a 20 mL vial is placed compound f (320 mg, 1.5 mmol, 1 equiv.), $K_2CO_3$ (245 mg, 1.8 mmol, 1.2 equiv.), and (S)-1-(3-trifluoromethyl-phenyl)-ethylamine in 5 mL of DMF. This was capped and heated at 95° C. for 16 h. The reaction is transferred to a separatory funnel, diluted with water/brine and extracted with EtOAc. The organics are dried over $Na_2SO_4$, filtered and evaporated. The residue is purified via flash chromatography (0-30% EtOAc/hept) to yield g and compound h. Compounds g and h are placed in 30 mL of AcOH and heated at 130° C. for 48 h. The AcOH is removed in vacuo and the residue partititoned between saturated $NaHCO_3$ and EtOAc. The organics are dried over $Na_2SO_4$, filtered and evaporated. The residue is then purified via flash chromatography (0-40% EtOAc/hept) to provide 173 mg (34%) of compound h as a yellow oil which was used without further purification.

Step 4: In a 50 mL flask is placed compound h (173 mg, 0.5 mmol, 1 equiv.) in 10 mL of $CH_2Cl_2$. To this is added mCPBA (75%, 234 mg, 1.02 mmol, 2 equiv.) in two equal portions and the reaction allowed to stir for 16 h. Another 180 mg of mCPBA are added in three 60 mg portions once per hour. After complete addition and 1 h of stirring, the reaction is diluted with MeOH and evaporated. The residue is then taken up in minimal DMSO and purified via HPLC. The desired fractions are then lyophilized to provide 81 mg (43%) of 1,1-dioxo-4-[(S)-1-(3-trifluoromethyl-phenyl)-ethyl]-1,4-dihydro-2H-1-1ambda*6*-pyrazino[2,3-b][1,4]thiazin-3-one (Compound I-22) as a pale yellow foam. LC/MS Rt=0.91 min; [M+H]$^+$=371.9.

The following compounds were prepared in a similar manner:

TABLE 3

| Compound number | R | Rt (min) | HPLC Method | M$^+$ |
|---|---|---|---|---|
| I-23 | (2-trifluoromethoxy-3-fluorophenyl) | 0.92 | 1 | 391.9 |
| I-24 | (3-trifluoromethylphenyl) | 0.90 | 1 | 357.0 |

Scheme 4

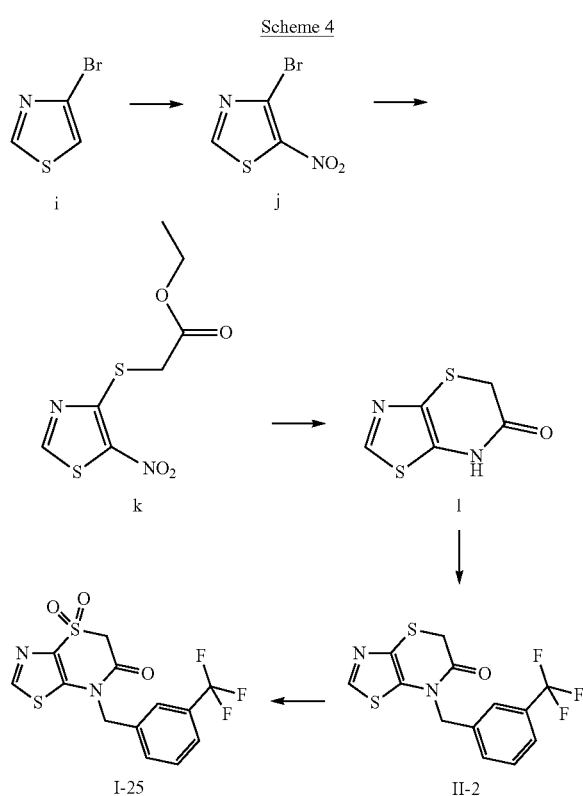

General Procedure 3 for the Preparation of Thiazole and Thiophene Fused Thiazinones Preparation of 7-(3-trifluoromethyl-benzyl)-7H-thiazolo[4,5-b][1,4]thiazin-6-one (Compound II-2) and 4,4-dioxo-7-(3-trifluoromethyl-benzyl)-4,7-dihydro-5H-4lambda*6*-thiazolo[4,5-b][1,4]thiazin-6-one (Compound I-25).

Step 1: In a 250 mL flask is placed compound i (5.0 g, 9.6 mmol) in 40 mL of $H_2SO_4$. This is then cooled to 0° C. where 8 mL of fuming nitric acid is added dropwise. The reaction is equipped with a condenser and heated at 60° C. for 16 h. Reaction is cooled to room temperature and poured into 300 mL of ice. Once the ice is melted, the white foam was filtered through a frit. The solids were allowed to dry and are then placed on the lyophilizer for 18 h to provide 2 g (31%) of compound j as a pale yellow solid.

Step 2: In a 50 mL flask is placed ethyl thioglycolate (592 mg, 4.9 mmol, 1.03 equiv.) in 10 mL of DMF. To this solution is added sodium hydride (60% dispersion, 201 mg, 5.0 mmol, 1.05 equiv.). After gas evolution, compound j (1.0 g, 4.8 mmol, 1 equi.v) is added and the reaction allowed to stir for 30 minutes. The volatiles are removed and the residue is purified via flash chromatography (0-50% EtOAc/hept) to provide 800 mg (67%) of compound k as a yellow solid.

Step 3: In a 250 mL flask is placed compound k (800 mg, 3.2 mmol) in 20 mL of AcOH. To this is added iron powder (360 mg, 6.4 mmol, 3 equiv.) and the reaction is allowed to stir at room temperature for 2 h at which point it is heated at 70° C. for 16 h. The reaction is filtered through Celite and the filtrate evaporated. The residue is then sonicated with water and filtered to provide 300 mg (57%) of the crude product compound 1 which is used without further purification.

Step 4: In a 50 mL flask is placed compound 1 (100 mg, 0.6 mmol, 1.0 equiv.) in 5 mL of DMF. To this solution is added sodium hydride (60% dispersion, 26.6 mg, 0.7 mmol, 1.1 equiv.) and this is allowed to stir for 10 mins. 3-Trifluoromethylbenzyl bromide (153 mg, 0.6 mmol, 1.1 equiv.) is added and the reaction allowed to stir at room temperature for 4 h. Reaction is transferred to separatory funnel with water (50 mL total) and extracted with EtOAc (2×25 mL). Organics were dried over $Na_2SO_4$, filtered, and evaporated. The residue is purified via flash chromatography (0-30% EtOAc/hept) to provide 116 mg of compound II-2 which was used without further purification, LC/MS, method 1: Rt=0.90 min.; [M+H]$^+$=331.4.

Step 5: In a 20 ml vial is placed compound II-2 (100 mg, 0.3 mmol, 1 equiv.) in 5 mL of $CH_2Cl_2$. To this is added mCPBA (131 mg, 0.8 mmol, 2.5 equiv.) and the reaction allowed to stir for 4 h. The crude reaction was then loaded on a flash column and purified using 0-70% EtOAc/hept as an eluent. The desired fractions combined and concentrated to provide 44 mg (40%) of 4,4-dioxo-7-(3-trifluoromethyl-benzyl)-4,7-dihydro-5H-4lambda*6*-thiazolo[4,5-b][1,4]thiazin-6-one (Compound I-25) as a white solid. LC/MS, method 1: Rt=0.82 min.; [M+H]$^+$=363.4.

The following compounds were prepared in a similar manner:

TABLE 4

| Compound number | R1 | R2 | Rt (min) | HPLC Method | M$^+$ |
|---|---|---|---|---|---|
| I-26 | ![R1-26] (3,4-difluoro-2-(difluoromethoxy)benzyl) | H | 0.87 | 1 | 396.9 |
| I-27 | ![R1-27] (3,4-difluoro-2-(difluoromethoxy)benzyl) | Me | 0.92 | 1 | 410.8 |
| I-28 | ![R1-28] (3-(trifluoromethyl)benzyl) | Me | 0.89 | 1 | 376.8 |

TABLE 4-continued

Structure: thiazole fused ring with SO₂, N-R1, S, R2 substituents

| Compound number | R1 | R2 | Rt (min) | HPLC Method | M⁺ |
|---|---|---|---|---|---|
| I-29 | (3-OCF₃-phenyl) | Me | 0.92 | 1 | 392.8 |
| I-30 | (3-CF₃-phenyl) | cyclopropyl | 0.94 | 1 | 403.4 |
| I-31 | (3-OCF₃-phenyl) | H | 0.85 | 1 | 379.4 |
| I-32 | (3-CF₃-phenyl with methyl) | H | 0.86 | 1 | 377.4 |

Scheme 5

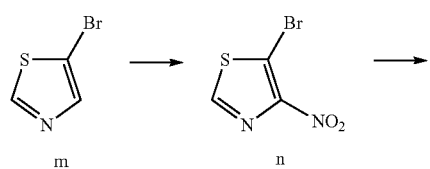

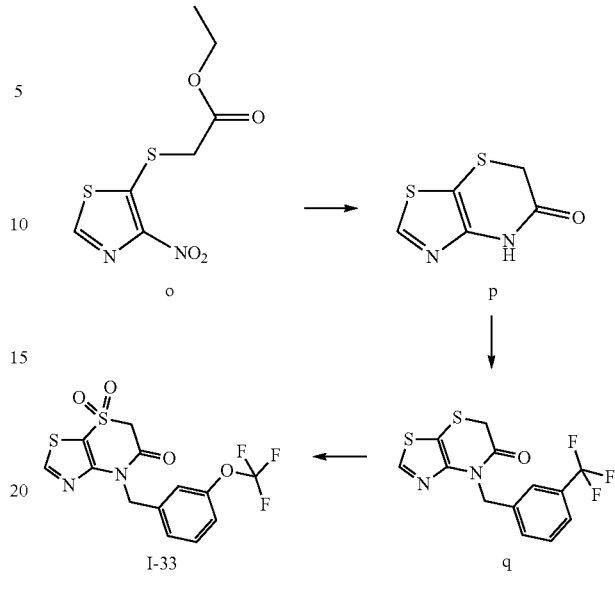

Compound I-33 through I-37 are prepared using General Procedure 3 with compound m used in place of compound i according to Scheme 5. Compounds prepared similarly are found in Table 5.

TABLE 5

| Compound number | R1 | R2 | Rt (min) | HPLC Method | M⁺ |
|---|---|---|---|---|---|
| I-33 | (3-OCF₃-4-F-phenyl) | H | 0.93 | 1 | 396.9 |
| I-34 | (3-OCF₃-4-F-phenyl) | isopropyl | 1.15 | 1 | 438.9 |
| I-35 | (3-CF₃-phenyl) | isopropyl | 1.10 | 1 | 404.9 |

TABLE 5-continued

![structure]

| Compound number | R1 | R2 | Rt (min) | HPLC Method | M+ |
|---|---|---|---|---|---|
| I-36 | 3-(OCF3)phenyl | iPr | 1.12 | 1 | 420.9 |
| I-37 | 3-(CF3)phenyl | Me | 0.96 | 1 | 376.8 |

Compounds I-38 and I-39 were prepared using General Procedure 3 with 3-bromo-2-nitrothiophene used in place of compound j.

TABLE 6

![structure]

| Compound number | R | Rt (min) | HPLC Method | M+ |
|---|---|---|---|---|
| I-38 | 1-(3-(CF3)phenyl)ethyl | 0.97 | 1 | 375.5 |
| I-39 | 3-(OCF3)-4-fluorophenyl | 0.93 | 1 | 396.3 |

Compounds I-40 through I-43 were prepared using General Procedure 3 with 2-chloro-3-nitrothiophene used in place of compound compound j.

TABLE 7

![structure]

| Compound number | R1 | R2 | Rt (min) | HPLC Method | M+ |
|---|---|---|---|---|---|
| I-40 | 3-(OCF3)-4-fluorophenyl | H | 0.92 | 1 | 396.3 |
| I-41 | 3-(CF3)phenyl | CH2CO2Me | 0.95 | 1 | 420.4 |
| I-42 | 3-(OCF3)phenyl | CH2CO2Me | 0.98 | 1 | 436.4 |
| I-43 | 1-(3-(CF3)phenyl)ethyl | CH2CO2Me | 0.99 | 1 | 434.4 |

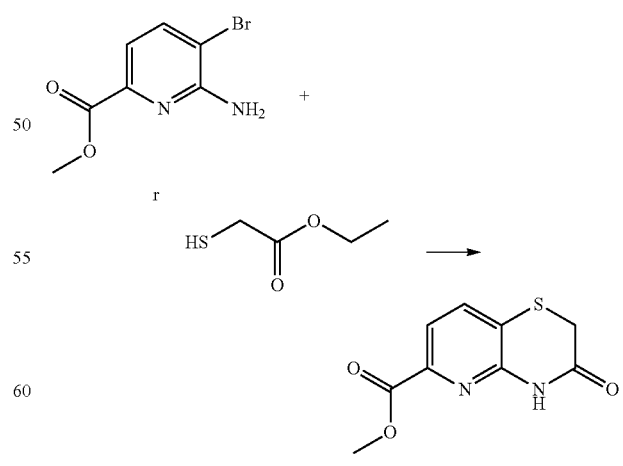

Scheme 6

Preparation of 3-Oxo-3,4-dihydro-2H-pyrido[3,2-b][1,4]thiazine-6-carboxylic acid methyl ester (s).

Ethyl thioglycolate is placed in a 50 mL flask in 5 mL of DMF and cooled to 0° C. Sodium hydride is added (60% dispersion, 95 mg, 1.4 mmol, 1.1 equiv.) and the reaction is allowed to stir for 25 min. Compound r (300 mg, 1.3 mmol, 1 equiv.) is added and after 4 h the reaction is quenched by the addition of water and then extracted into EtOAc (2×20 mL). Organic extracts are combined and dried (MgSO$_4$) then concentrated. The residue is purified using flash chromatography (0-70% EtOAc/hept). The desired product fractions are combined and concentrated to provide 93 mg of compound s.

Scheme 7

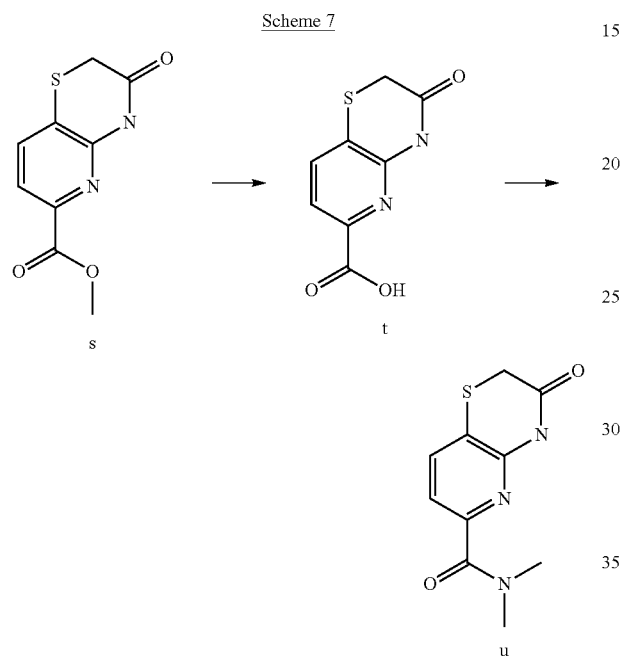

Scheme 8

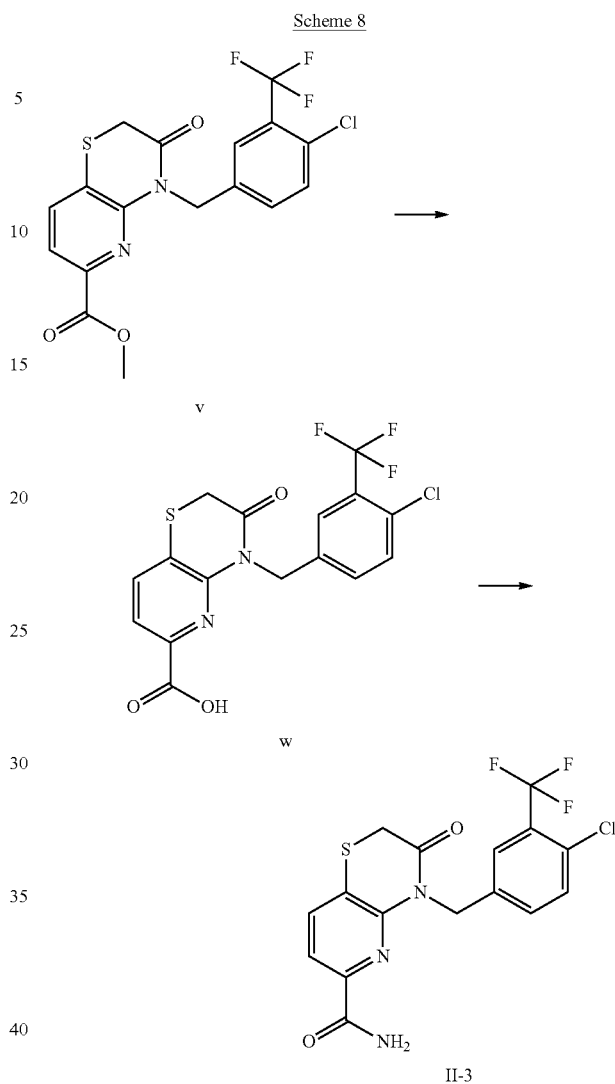

Preparation of 3-Oxo-3,4-dihydro-2H-pyrido[3,2-b][1,4] thiazine-6-carboxylic acid (t). Compound s (250 mg, 1.1 mmol, 1 equiv.) is placed in 20 mL of dioxane and 5 mL of water. Aqueous 0.5 M sodium hydroxide (2 mL) was added dropwise over 30 minutes. The reaction is allowed to stir (23° C./16 h). The volatiles are removed to a volume of ~3 mL to which is then added 5 mL water and the mixture acidified to pH 4 with 1M HCl. The resulting precipitate was filtered and dried to provide 190 mg of the desired product (t). LC/MS Rt=0.39 min.; [M+H]$^+$=211.4.

Preparation of N,N-dimethyl-3-oxo-3,4-dihydro-2H-pyrido[3,2-b][1,4]thiazine-6-carboxylic acid amide (u).

Compound t (180 mg, 0.9 mmol, 1 equiv.) is placed in a 20 mL vial with 10 mL of THF. Diisopropylethylamine (0.3 mL) and TBTU (314 mg, 1 mmol, 1.1 equi.v) are added and the mixture allowed to stir at room temperature for 10 minutes. Dimethylamine (2 M in THF, 0.6 mL, 1.2 equiv.) are added and the mixture let stir at room temperature for 1 h at which point 1 mL DMF is added and the mixture allowed to stir (~16 h/23° C.). Reaction is diluted with EtOAc (25 mL) and washed with water (2×20 mL). Organics are then dried (MgSO$_4$), filtered, and concentrated. The residue is purified on flash chromatography (30-100% EtOAc/hept) and the desired fractions are combined and concentrated to provide 160 mg of the desired product (u).

Preparation of 4-(4-chloro-3-trifluoromethyl-benzyl)-1,1, 3-trioxo-1,2,3,4-tetrahydro-11ambda*6*-pyrido[3,2-b][1,4] thiazine-6-carboxylic acid amide (Compound II-3).

Step 1: Compound v (prepared following similar methods as described for compound I-1, 800 mg, 1.9 mmol, 1 equiv.) is dissolved in 25 mL of dioxane and 5 mL of water. To this is added NaOH (0.5 M, 5 mL, 2.5 mmol, 1.3 equiv.) and the mixture allowed to stir at room temperature for 3 days. The reaction is concentrated and then added a small amount of water (~5 mL) was added. The mixture is made acidic with 1 M HCl. The resulting precipitate is filtered, washed with water, and dried to provide compound w which is used without further purification.

Step 2: Compound w (260 mg, 0.6 mmol, 1 equiv.) is suspended in ACN (5 mL) and then di-tert-butyl dicarbonate (183 mg, 0.8 mmol, 1.3 equiv.) is added. Pyridine (0.16 mL, 1.9 mmol, 3 equiv.) is added and the resulting slurry stirred for 15 minutes. NH$_4$HCO$_3$ (102 mg, 1.3 mmol, 2 equiv.) is added portionwise to the stirring solution and the resulting mixture is stirred overnight. The ACN is evaporated in vacuo to give a white yellow solid. The solid is triturated with 10% NaOH, filtered, and washed with water. The solids are then rinsed with 5% ether in petroleum ether and allowed to dry to provide the desired compound II-3 (140 mg), LC/MS, method 2: Rt=2.74 min.; [M+H]$^+$=402.7.

Compounds II-4 through II-23 shown in Table 8-Table 10 are prepared via General Procedures 1-3:

TABLE 8

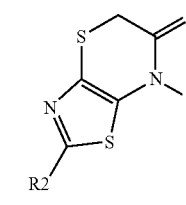

| Compound number | R1 | R2 | R3 | Rt (min) | HPLC Method | M$^+$ |
|---|---|---|---|---|---|---|
| II-4 | 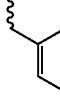 | H | H | 1.10 | 1 | 339.8 |
| II-5 |  | H | H | 1.15 | 1 | 359.1 |
| II-6 | 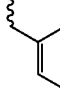 | H | H | 0.98 | 1 | 343.4 |
| II-7 | 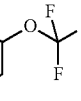 | H | H | 1.17 | 1 | 391.1 |
| II-8 | 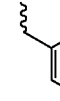 | H | H | 1.06 | 1 | 422.9 |
| II-9 | 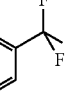 | H | Cl | 1.23 | 1 | 392.9 |
| II-10 |  | H | H | 1.09 | 1 | 336.0 |
| II-11 | 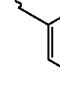 | HO 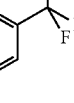 | H | 2.09 | 1 | 389.4 |

TABLE 9

| Compound number | R1 | R2 | Rt (min) | HPLC Method | M$^+$ |
|---|---|---|---|---|---|
| II-12 | 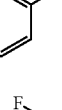 | Me | 1.01 | 1 | 360.8 |
| II-13 | 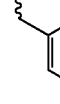 | H | 0.93 | 1 | 347.4 |
| II-14 | 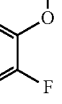 | 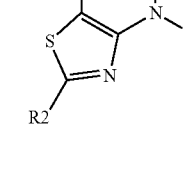 | 1.05 | 1 | 371.4 |
| II-15 | 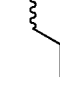 | Me | 0.90 | 1 | 345.3 |
| II-16 | 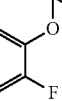 | H | 0.95 | 1 | 346.6 |
| II-17 |  | H | 0.95 | 1 | 364.9 |

TABLE 10

| Compound number | R1 | R2 | Rt (min) | HPLC Method | M$^+$ |
|---|---|---|---|---|---|
| II-18 |  |  | 1.29 | 1 | 407.7 |

TABLE 10-continued

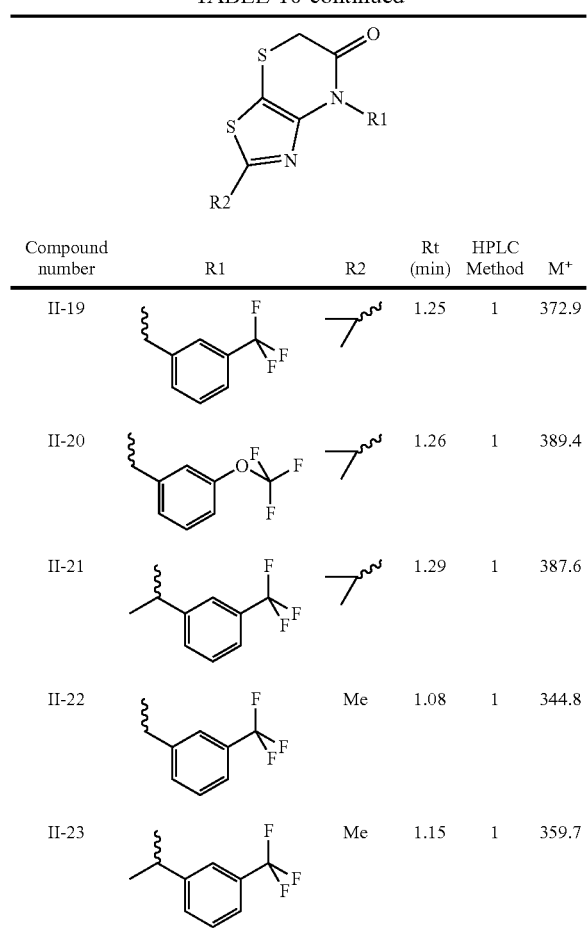

| Compound number | R1 | R2 | Rt (min) | HPLC Method | M+ |
|---|---|---|---|---|---|
| II-19 | 3-(trifluoromethyl)phenyl-CH2 | isopropyl | 1.25 | 1 | 372.9 |
| II-20 | 3-(trifluoromethoxy)phenyl-CH2 | isopropyl | 1.26 | 1 | 389.4 |
| II-21 | 1-(3-(trifluoromethyl)phenyl)ethyl | isopropyl | 1.29 | 1 | 387.6 |
| II-22 | 3-(trifluoromethyl)phenyl-CH2 | Me | 1.08 | 1 | 344.8 |
| II-23 | 1-(3-(trifluoromethyl)phenyl)ethyl | Me | 1.15 | 1 | 359.7 |

Description of Biological Properties
KCa3.1 Assay

HEK293 cells over-expressing human KCa3.1 are used to measure the effects of compounds in inhibiting the KCa3.1 channel function. The assay is based on measuring the influx of Tl+ through KCa3.1 using a FLIPR dye assay (FLIPR Potassium Ion Channel Assay Kit #R8154 by Molecular Devices). The day before the assay HEK293/KCa3.1 cells are seeded on a 384 well plate. On the day of the assay, media is removed and replaced with Molecular Devices Potassium Ion Channel dye then incubated for 1 hour according to manufacturer's recommendations. The cells are then treated with compounds or DMSO control for 15 min, followed by addition of thallium (final concentration=1.5 mM) and ionomycin (final concentration=1 uM). The plate is read on HAMAMATSU 60000 measuring fluorescence signal for 50 seconds using (Em: 565-625 nm). Data analysis: HAMAMATSU 6000 data are exported using max-min value for frame 10 and 40 and corrected by spatial uniformity correction. Percent of control (POC) is calculated as 100×(max-minFlsample−max-minFllow)/(max-minFlhi−max-minFllow). Max-min Flsample is max-min value of each sample well containing test compound. Max-min Fllow is average max-min value of wells containing reference inhibitory compound. Max-min Flhi is average max-min value of wells containing DMSO. IC50 values are determined by nonlinear curve fitting of the data from a duplicate 11-point concentration-response curve.

The following examples describe the biological activity of the compounds according to the invention.

| Compound number | KCa3.1 IC$_{50}$ (nM) |
|---|---|
| I-1 | 290 |
| I-2 | 120 |
| I-3 | 180 |
| I-4 | 140 |
| I-5 | 49 |
| I-6 | 5000 |
| I-7 | 350 |
| I-8 | 1900 |
| I-9 | 110 |
| I-10 | 180 |
| I-12 | 77 |
| I-13 | 830 |
| I-15 | 92 |
| I-16 | 2000 |
| I-17 | 350 |
| I-18 | 88 |
| I-19 | 2200 |
| I-20 | 490 |
| I-21 | 240 |
| I-22 | 1100 |
| I-23 | 170 |
| I-24 | 2600 |
| I-25 | 3700 |
| I-26 | 510 |
| I-27 | 310 |
| I-28 | 4000 |
| I-29 | 2400 |
| I-30 | 4300 |
| I-31 | 2200 |
| I-32 | 1000 |
| I-33 | 110 |
| I-34 | 96 |
| I-35 | 240 |
| I-36 | 380 |
| I-37 | 230 |
| I-38 | 71 |
| I-39 | 39 |
| I-40 | 48 |
| I-41 | 190 |
| I-42 | 150 |
| I-43 | 120 |
| II-1 | 52 |
| II-2 | 320 |
| II-3 | 180 |
| II-4 | 41 |
| II-5 | 46 |
| II-6 | 3600 |
| II-7 | 52 |
| II-8 | 47 |
| II-9 | 130 |
| II-10 | 310 |
| II-11 | 66 |
| II-12 | 260 |
| II-13 | 160 |
| II-14 | 1600 |
| II-15 | 490 |
| II-16 | 170 |
| II-17 | 60 |
| II-18 | 250 |
| II-19 | 340 |
| II-20 | 510 |
| II-21 | 400 |
| II-22 | 73 |
| II-23 | 67 |

Therapeutic Use

On the basis of their biological properties the compounds of formula (I) & (II) according to the invention, or their tautomers, racemates, enantiomers, diastereomers, mixtures thereof and the salts of all the above-mentioned forms are suitable for treating diseases related to KCa3.1.

Such diseases include for example: rheumatoid arthritis, psoriasis, atherosclerosis, systemic lupus erythematosus, Crohn's disease, ulcerative colitis, multiple sclerosis, scleroderma, glomerulonephritis, chronic obstructive pulmonary disease and asthma including allergic asthma;

inflammatory bowel disease, graft versus host disease, Alzheimer's disease (Halks-Miller et al. (2003) Ann Neurol 54 p.638), chronic kidney disease;

bone resorption diseases including osteoporosis;

type 1 and type 2 diabetes;

lymphomas which include, but are not limited to AIDS-related lymphoma, non-Hodgkin's lymphoma, Hodgkins lymphoma, cutaneous T-cell lymphoma, and lymphoma of the central nervous system.

leukemias which include, but are not limited to acute myeloid leukemia, acute lymphoblastic leukemia, chronic;

osteoporosis, sickle cell disease, restenosis, periodontal disease, resterosis, renal fiborsis, lung fibrosis, liver fibrosis.

The compounds of formula (I) & (II) may be used on their own or in combination with other active substances according to the invention, optionally also in combination with other pharmacologically active substances.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with to known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose), emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may of course contain, apart from the above-mentioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

All patent and non-patent documents or literature cited in this application are herein incorporated by reference in their entirety.

The invention claimed is:

1. A compound of formula (I)

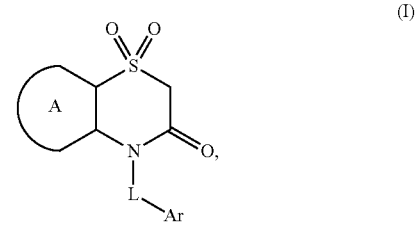

(I)

wherein
ring A

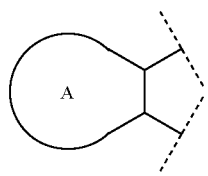

is fused to the 1,1-dioxothiazinone ring and chosen from

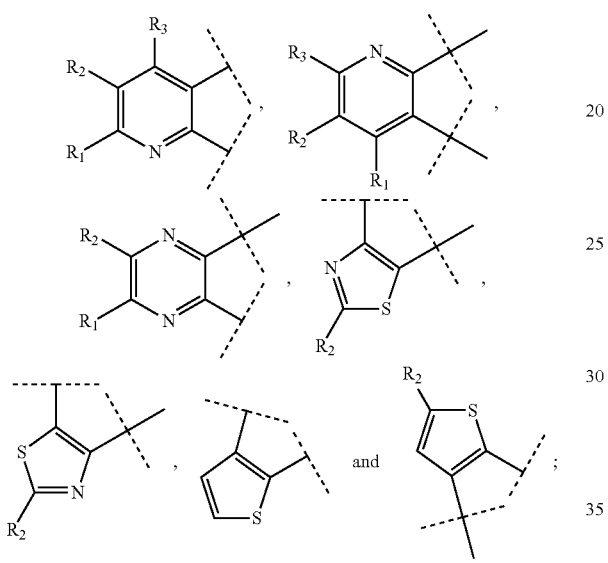

L is a bond or —(CH$_2$)$_n$— wherein one or more methylene hydrogens is optionally replaced by C$_{1-5}$alkyl, C$_{2-6}$alkenyl, C$_{2-6}$alkynyl or C$_{1-5}$haloalkyl;
n is 1 to 3;
Ar is aryl or heteroaryl substituted independently by one or more halogen, C$_{1-6}$haloalkyl, C$_{1-6}$haloalkoxy or C$_{1-6}$haloalkylS(O)$_m$— and Ar is optionally further substituted by C$_{1-6}$alkyl;
m is 0, 1 or 2;
each R$^1$, R$^2$ and R$^3$ are independently chosen from hydrogen, halogen, C$_{1-5}$alkyl, C$_{3-6}$cycloalkyl, C$_{1-5}$alkyl-OH, —C(O)OR$^4$, —C(O)NR$^4$R$^4$, C$_{2-6}$alkenyl, C$_{2-6}$alkynyl, C$_{1-5}$haloalkyl, —OR$^4$ —NR$^4$R$^4$, —CN, —SR$^4$, —S(O)$_2$R$^4$, —S(O)$_2$NR$^4$R$^4$, —NHC(O)R$^4$ and —N(C$_{1-4}$alkyl)C(O)OR$^4$;
each R$^4$ is independently hydrogen, or C$_{1-6}$alkyl;
or a pharmaceutically acceptable salt thereof.

2. The compound according to claim 1 wherein
L is a bond or —(CH$_2$)$_n$— wherein one or two methylene hydrogens is optionally replaced by C$_{1-3}$alkyl;
n is 1 or 2;
Ar is phenyl or heteroaryl chosen from furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl, each Ar is substituted independently by one or more halogen, C$_{1-5}$haloalkyl, C$_{1-5}$haloalkoxy or C$_{1-5}$haloalkylS(O)$_m$— and Ar is optionally further substituted by C$_{1-3}$alkyl;
m is 2;
each R$^1$, R$^2$ and R$^3$ are independently chosen from hydrogen, halogen, C$_{1-3}$alkyl, C$_{3-5}$cycloalkyl, C$_{1-3}$alkyl-OH, —C(O)OR$^4$, and —C(O)NR$^4$R$^4$;
each R$^4$ is independently hydrogen or C$_{1-3}$alkyl;
or a pharmaceutically acceptable salt thereof.

3. The compound according to claim 2 and wherein
L is a bond or —(CH$_2$)$_n$— wherein one methylene hydrogen is optionally replaced by methyl;
n is 1 or 2;
Ar is phenyl or heteroaryl chosen from pyrazolyl, and pyridyl, each Ar is substituted independently by one or more halogen, C$_{1-3}$haloalkyl, C$_{1-3}$haloalkoxy or C$_{1-3}$haloalkylS(O)$_m$—and Ar is optionally further substituted by C$_{1-3}$alkyl;
m is 2;
each R$^1$, R$^2$ and R$^3$ are independently chosen from hydrogen, halogen, C$_{1-3}$alkyl, C$_{3-5}$cycloalkyl, C$_{1-3}$alkyl-OH, —C(O)OR$^4$, and —C(O)NR$^4$R$^4$;
each R$^4$ is independently hydrogen or C$_{1-3}$alkyl;
or a pharmaceutically acceptable salt thereof.

4. The compound according to claim 3 and wherein
Ar is phenyl or heteroaryl chosen from pyrazolyl, and pyridyl, each Ar is substituted independently by one or more Cl, F, Br, CF$_3$, —OCF$_3$ or —S(O)$_2$—CF$_3$ and Ar is optionally further substituted by methyl;
each R$^1$, R$^2$ and R$^3$ are independently chosen from hydrogen, halogen, C$_{1-3}$alkyl, C$_{3-5}$cycloalkyl, C$_{1-3}$alkyl-OH, —C(O)OR$^4$, and —C(O)NR$^4$R$^4$;
each R$^4$ is independently hydrogen or methyl;
or a pharmaceutically acceptable salt thereof.

5. The compound according to claim 4 and wherein
ring A

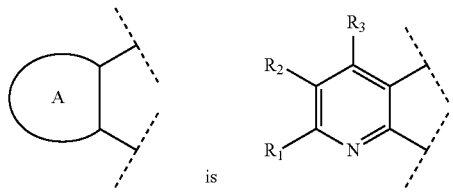

R$^1$ is hydrogen, —C(O)$_2$—CH$_3$, —C(O)—N(CH$_3$)$_2$ or —C(O)—NH$_2$;
R$^2$ is hydrogen or Cl;
R$^3$ is hydrogen;
or a pharmaceutically acceptable salt thereof.

6. The compound according to claim 4 and wherein
ring A

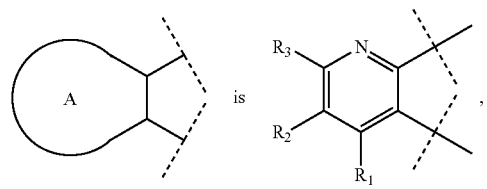

R$^1$ is hydrogen;
R$^2$ is Br;
R$^3$ is hydrogen;
or a pharmaceutically acceptable salt thereof.

7. The compound according to claim 4 and wherein ring A

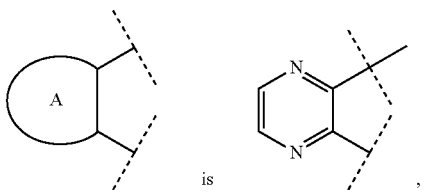

is

Ar is phenyl substituted independently by one or two F, CF₃ or —OCF₃;
or a pharmaceutically acceptable salt thereof.

8. The compound according to claim 4 and wherein ring A

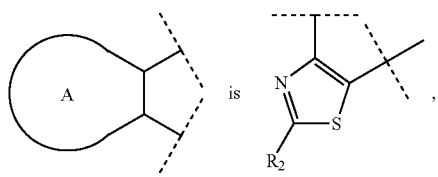

is

R₂ is hydrogen, methyl or cyclopropyl;
or a pharmaceutically acceptable salt thereof.

9. The compound according to claim 4 and wherein ring A

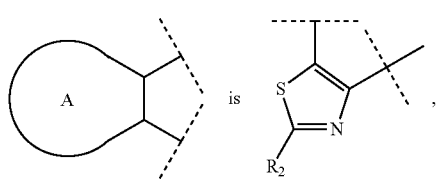

is

R₂ is hydrogen, methyl or isopropyl;
or a pharmaceutically acceptable salt thereof.

10. The compound according to claim 4 and wherein ring A

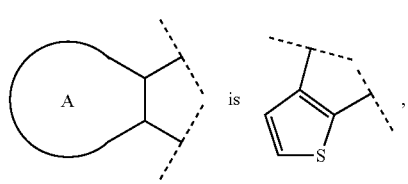

is or a pharmaceutically acceptable salt thereof.

11. The compound according to claim 4 and wherein ring A

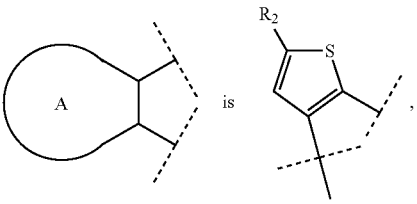

is

R₂ is hydrogen or —CO₂—CH₃,
or a pharmaceutically acceptable salt thereof.

12. The compound according to claim 5 and wherein the combination of L-Ar is

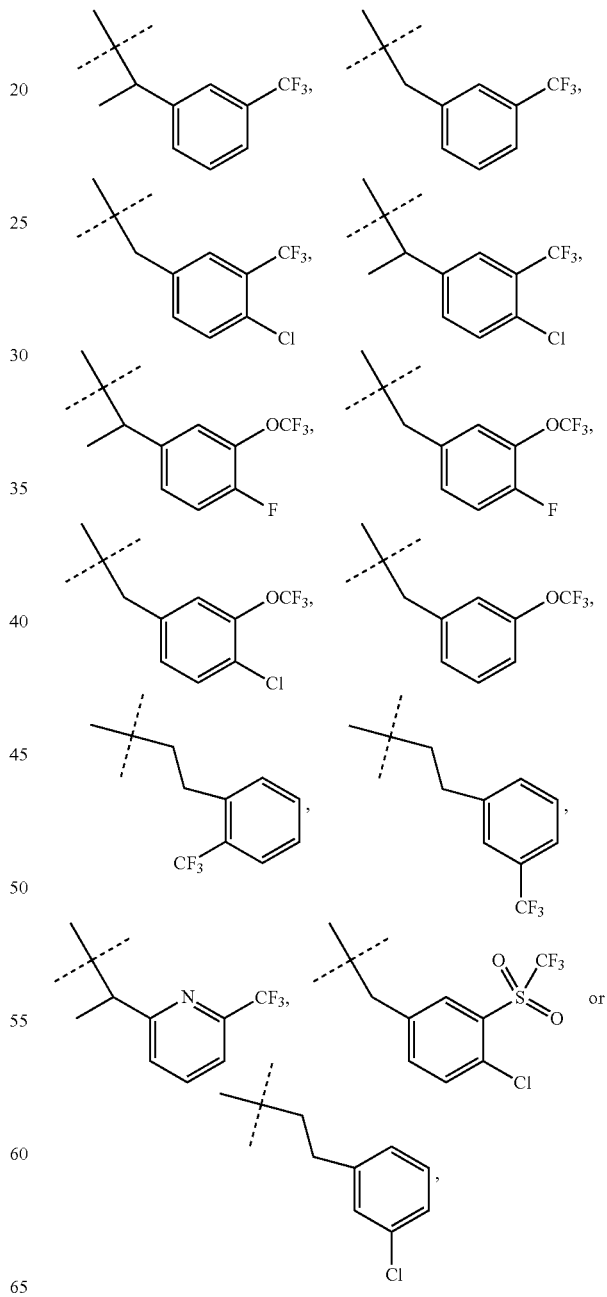

or a pharmaceutically acceptable salt thereof.

13. The compound according to claim 5 and wherein the combination of L-Ar is
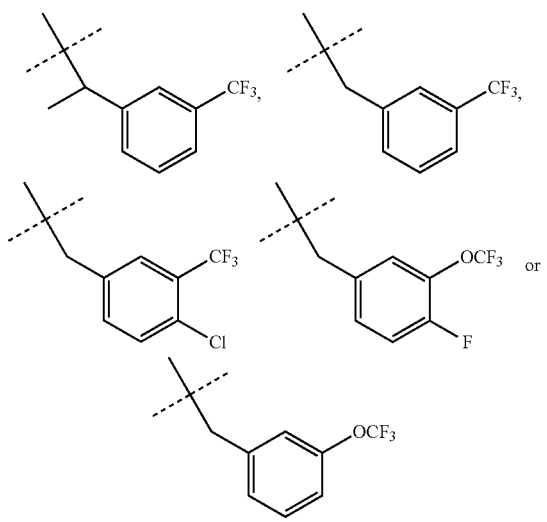
or a pharmaceutically acceptable salt thereof.
14. The compound according to claim 5 and wherein the combination of L-Ar is
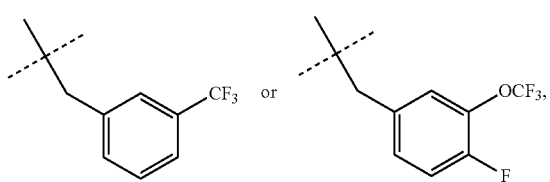
or a pharmaceutically acceptable salt thereof.
15. A compound chosen from the group identified below -continued

| Compound number | Structure |
|---|---|
| I-12 | 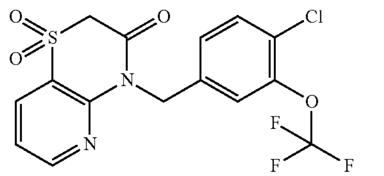 [SMILES: O=C1CS(=O)(=O)c2cccnc2N1Cc1ccc(Cl)c(OC(F)(F)F)c1] |
| I-13 | 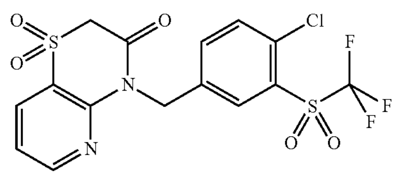 [SMILES: O=C1CS(=O)(=O)c2cccnc2N1Cc1ccc(Cl)c(S(=O)(=O)C(F)(F)F)c1] |
| I-15 | 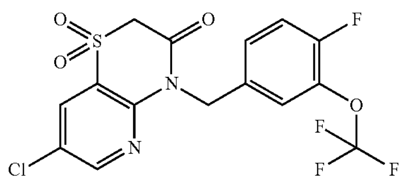 [SMILES: O=C1CS(=O)(=O)c2cc(Cl)cnc2N1Cc1ccc(F)c(OC(F)(F)F)c1] |
| I-16 | 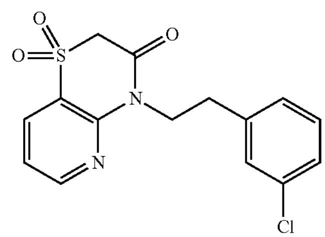 [SMILES: O=C1CS(=O)(=O)c2cccnc2N1CCc1cccc(Cl)c1] |
| I-17 | 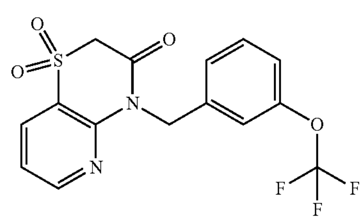 |
| I-18 | 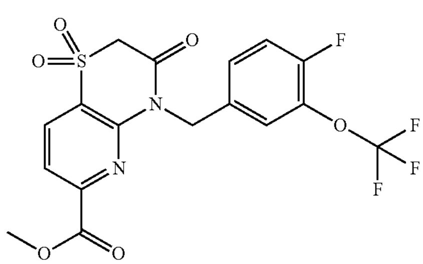 [SMILES: COC(=O)c1ccc2c(n1)N(Cc1ccc(F)c(OC(F)(F)F)c1)C(=O)CS2(=O)=O] |
| I-19 | 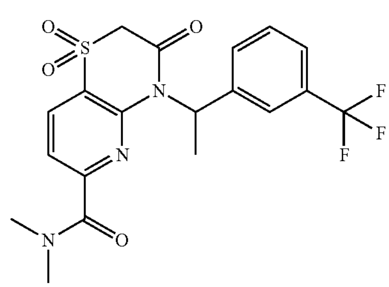 [SMILES: CC(c1cccc(C(F)(F)F)c1)N1C(=O)CS(=O)(=O)c2ccc(C(=O)N(C)C)nc21] |

-continued

| Compound number | Structure |
|---|---|
| I-20 | 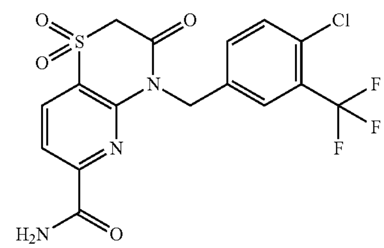 [SMILES: NC(=O)c1ccc2c(n1)N(Cc1ccc(Cl)c(C(F)(F)F)c1)C(=O)CS2(=O)=O] |
| I-21 | 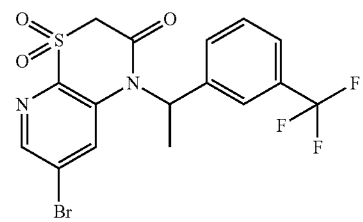 [SMILES: CC(c1cccc(C(F)(F)F)c1)N1C(=O)CS(=O)(=O)c2ncc(Br)cc21] |
| I-22 | 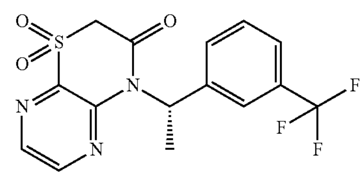 [SMILES: C[C@@H](c1cccc(C(F)(F)F)c1)N1C(=O)CS(=O)(=O)c2nccnc21] |
| I-23 | 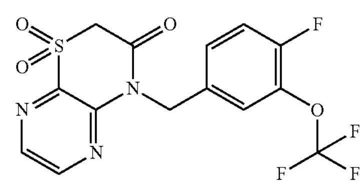 [SMILES: O=C1CS(=O)(=O)c2nccnc2N1Cc1ccc(F)c(OC(F)(F)F)c1] |
| I-24 | 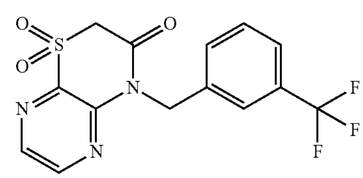 [SMILES: O=C1CS(=O)(=O)c2nccnc2N1Cc1cccc(C(F)(F)F)c1] |
| I-25 | 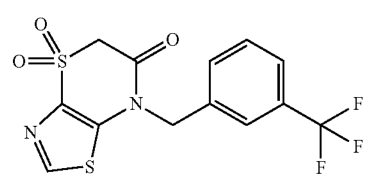 [SMILES: O=C1CS(=O)(=O)c2ncsc2N1Cc1cccc(C(F)(F)F)c1] |
| I-26 | 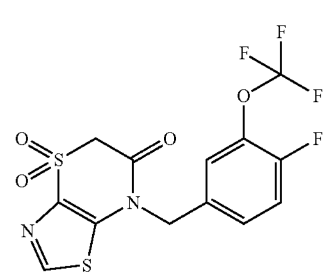 [SMILES: O=C1CS(=O)(=O)c2ncsc2N1Cc1ccc(F)c(OC(F)(F)F)c1] |

| Compound number | Structure |
|---|---|
| I-27 | 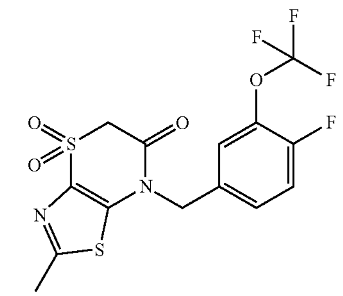 [SMILES: Cc1nc2c(s1)N(Cc1ccc(F)c(OC(F)(F)F)c1)C(=O)CS2(=O)=O] |
| I-28 | 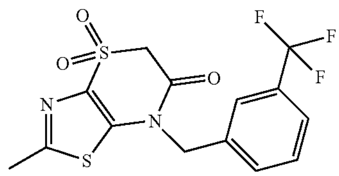 [SMILES: Cc1nc2c(s1)N(Cc1cccc(C(F)(F)F)c1)C(=O)CS2(=O)=O] |
| I-29 | 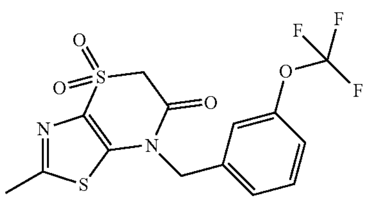 [SMILES: Cc1nc2c(s1)N(Cc1cccc(OC(F)(F)F)c1)C(=O)CS2(=O)=O] |
| I-30 | 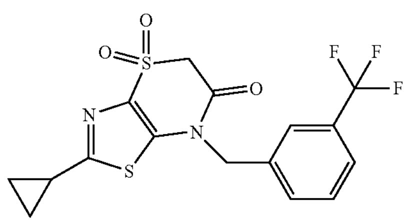 [SMILES: O=C1CS(=O)(=O)c2nc(C3CC3)sc2N1Cc1cccc(C(F)(F)F)c1] |
| I-31 | 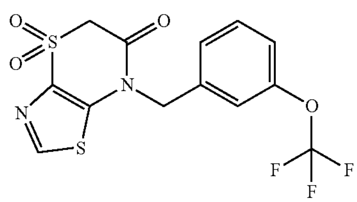 [SMILES: O=C1CS(=O)(=O)c2ncsc2N1Cc1cccc(OC(F)(F)F)c1] |
| I-32 | 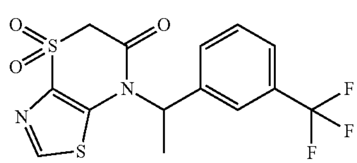 [SMILES: CC(c1cccc(C(F)(F)F)c1)N1C(=O)CS(=O)(=O)c2ncsc21] |
| I-33 | 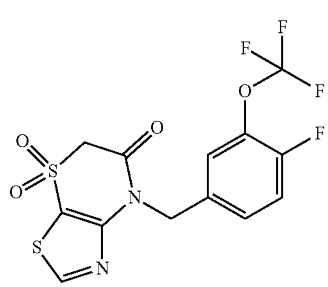 [SMILES: O=C1CS(=O)(=O)c2scnc2N1Cc1ccc(F)c(OC(F)(F)F)c1] |

| Compound number | Structure |
|---|---|
| I-34 | 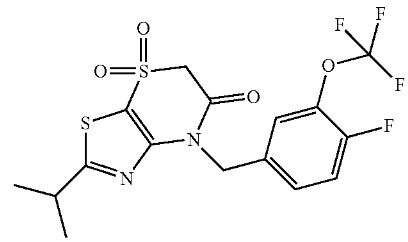 [SMILES: CC(C)c1nc2c(s1)S(=O)(=O)CC(=O)N2Cc1ccc(F)c(OC(F)(F)F)c1] |
| I-35 | 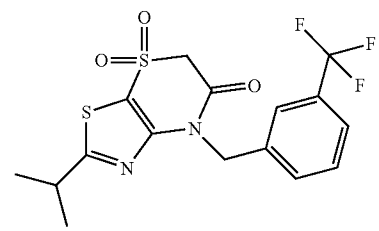 [SMILES: CC(C)c1nc2c(s1)S(=O)(=O)CC(=O)N2Cc1cccc(C(F)(F)F)c1] |
| I-36 | 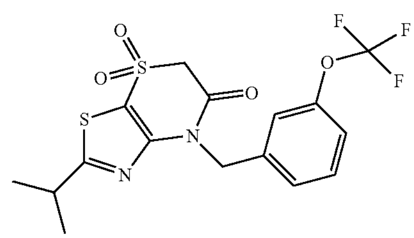 [SMILES: CC(C)c1nc2c(s1)S(=O)(=O)CC(=O)N2Cc1cccc(OC(F)(F)F)c1] |
| I-37 | 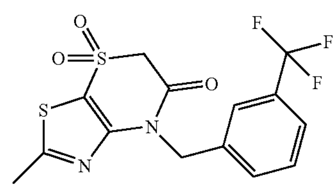 [SMILES: Cc1nc2c(s1)S(=O)(=O)CC(=O)N2Cc1cccc(C(F)(F)F)c1] |
| I-38 | 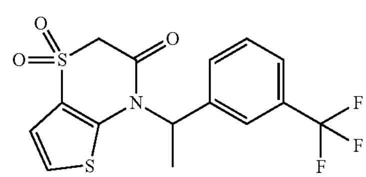 [SMILES: CC(c1cccc(C(F)(F)F)c1)N1C(=O)CS(=O)(=O)c2ccsc21] |
| I-39 | 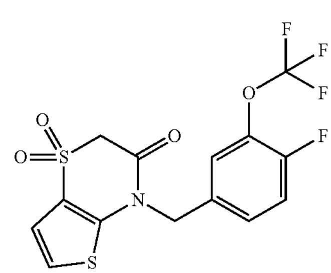 [SMILES: O=C1CS(=O)(=O)c2ccsc2N1Cc1ccc(F)c(OC(F)(F)F)c1] |

-continued

| Compound number | Structure |
|---|---|
| I-40 | 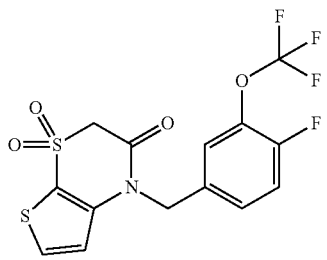 [SMILES: O=C1CS(=O)(=O)c2sccc2N1Cc1ccc(F)c(OC(F)(F)F)c1] |
| I-41 | 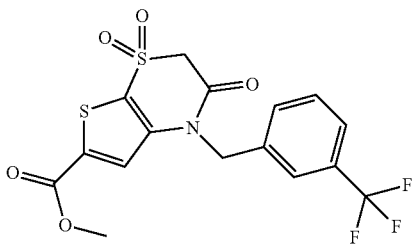 [SMILES: COC(=O)c1cc2c(s1)S(=O)(=O)CC(=O)N2Cc1cccc(C(F)(F)F)c1] |
| I-42 | 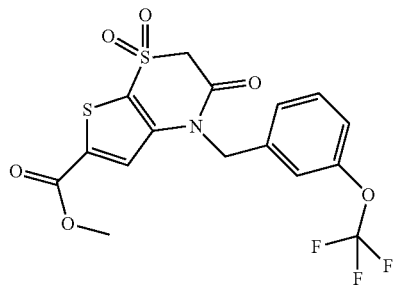 [SMILES: COC(=O)c1cc2c(s1)S(=O)(=O)CC(=O)N2Cc1cccc(OC(F)(F)F)c1] |
| I-43 | 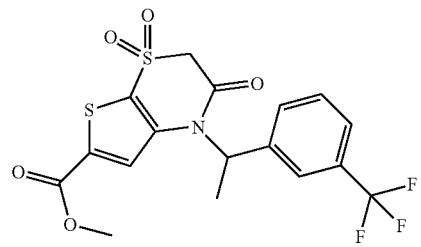 | or a pharmaceutically acceptable salt thereof.

16. A compound of formula (II)

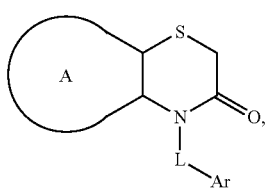

(II)

wherein
ring A

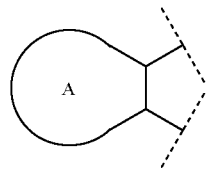

is fused to the 1,1-dioxothiazinone ring and chosen from

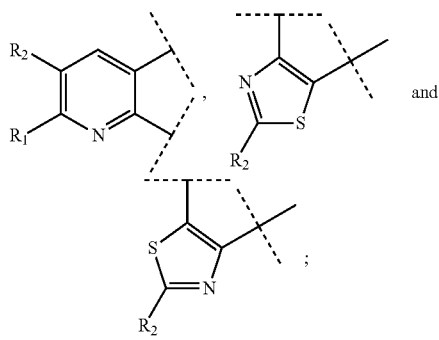

L is a bond or —(CH$_2$)$_n$— wherein one or more methylene hydrogens is optionally replaced by C$_{1-5}$alkyl, C$_{2-6}$alkenyl, C$_{2-6}$alkynyl or C$_{1-5}$haloalkyl;
n is 1 to 3;
Ar is aryl or heteroaryl substituted independently by one or more halogen, C$_{1-5}$haloalkyl, C$_{1-5}$haloalkoxy or C$_{1-5}$haloalkylS(O)$_m$— and optionally further substituted by C$_{1-5}$alkyl;
m is 0, 1 or 2;
each R$^1$, R$^2$ are independently chosen from hydrogen, halogen, C$_{1-5}$alkyl, C$_{3-6}$cycloalkyl, C$_{1-5}$alkyl-OH, —C(O)OR$^3$, —C(O)NR$^3$R$^3$, C$_{2-6}$alkenyl, C$_{2-6}$alkynyl, C$_{1-5}$haloalkyl, —NR$^3$R$^3$, —CN, —S(O)$_2$R$^3$, —S(O)$_2$NR$^3$R$^3$, —NHC(O)R$^3$ and —N(C$_{1-4}$alkyl)C(O)R$^3$;
each R$^3$ is independently hydrogen or C$_{1-5}$alkyl;
or a pharmaceutically acceptable salt thereof.

17. The compound according to claim 16 and wherein
L is a bond or —(CH$_2$)$_n$— wherein one or two methylene hydrogens is optionally replaced by C$_{1-3}$alkyl;
n is 1 or 2;
Ar is phenyl or heteroaryl chosen from furyl, thienyl, pyrrolyl, oxazolyl, thiazolyl, isoxazolyl, isothiazolyl, pyrazolyl, imidazolyl, triazolyl, tetrazolyl, oxadiazolyl, thiadiazolyl, pyridyl, pyrimidyl, pyridazinyl, pyrazinyl and triazinyl, each Ar is substituted independently by one or more halogen, C$_{1-5}$haloalkyl, C$_{1-6}$haloalkoxy or C$_{1-5}$haloalkylS(O)$_m$— and Ar is optionally further substituted by C$_{1-3}$alkyl;
m is 0 or 2;
each R$^1$, R$^2$ are independently chosen from hydrogen, halogen, C$_{1-3}$alkyl, C$_{3-5}$cycloalkyl, C$_{1-3}$alkyl-OH, and —C(O)NR$^3$R$^3$;
each R$^3$ is independently hydrogen or C$_{1-3}$ alkyl;
or a pharmaceutically acceptable salt thereof.

18. The compound according to claim 17 and wherein
L is a bond or —(CH$_2$)$_n$— wherein one methylene hydrogen is optionally replaced by methyl;
n is 1 or 2;
Ar is phenyl or heteroaryl chosen from pyrazolyl and pyridyl, each Ar is substituted independently by one or more halogen, C$_{1-3}$haloalkyl, C$_{1-3}$haloalkoxy or C$_{1-3}$haloalkylS(O)$_m$— and Ar is optionally further substituted by C$_{1-3}$alkyl;
m is 0 or 2;
each R$^1$, R$^2$ are independently chosen from hydrogen, halogen, C$_{1-3}$alkyl, C$_{3-5}$cycloalkyl, C$_{1-3}$alkyl-OH and —C(O)NR$^3$R$^3$;
each R$^3$ is independently hydrogen or C$_{1-3}$alkyl;
or a pharmaceutically acceptable salt thereof.

19. The compound according to claim 18 and wherein
Ar is phenyl or pyrazolyl, each Ar is substituted independently by one or more Cl, F, Br, CF$_3$, —OCF$_3$ or —S(O)$_2$—CF$_3$ and Ar is optionally further substituted by methyl;
each R$^1$, R$^2$ are independently chosen from hydrogen, halogen, C$_{1-3}$alkyl, C$_{3-5}$cycloalkyl, C$_{1-3}$alkyl-OH and —C(O)NR$^3$R$^3$;
each R$^3$ is independently hydrogen or methyl;
or a pharmaceutically acceptable salt thereof.

20. The compound according to claim 19 and wherein ring A

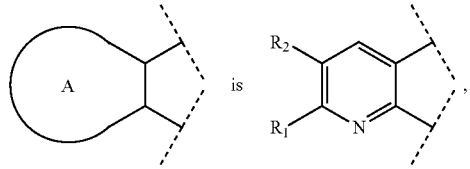

R$^1$ is hydrogen, C$_{1-3}$alkyl-OH, C$_{1-3}$alkyl, C$_{3-5}$cycloalkyl or —C(O)—NH$_2$;
R$^2$ is hydrogen or Cl;
or a pharmaceutically acceptable salt thereof.

21. The compound according to claim 19 and wherein ring A

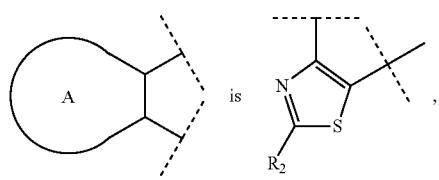

R$_2$ is hydrogen, methyl or cyclopropyl;
or a pharmaceutically acceptable salt thereof.

22. The compound according to claim 19 and wherein ring A

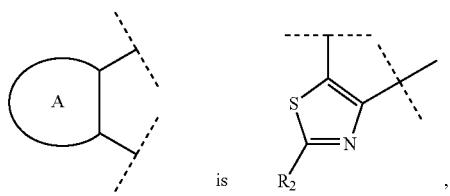

R$_2$ is methyl or isopropyl;
or a pharmaceutically acceptable salt thereof.

23. The compound according to claim 20, wherein the combination of L-Ar is

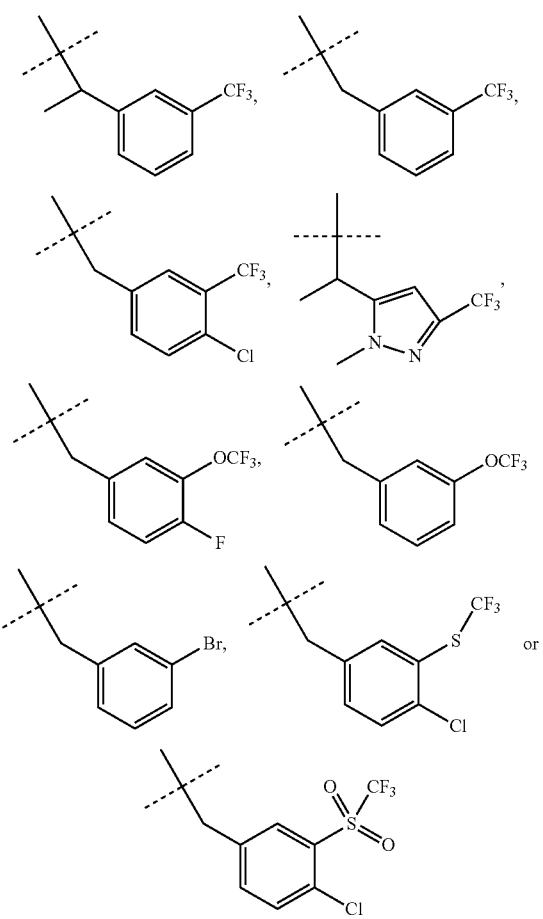

or a pharmaceutically acceptable salt thereof.

24. A compound chosen from the group identified below

| Compound number | Structure |
|---|---|
| II-1 | 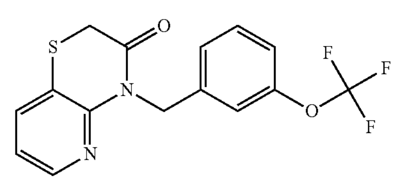 [SMILES: O=C1CSc2cccnc2N1Cc1cccc(OC(F)(F)F)c1] |
| II-2 | 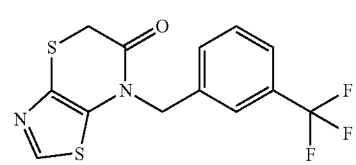 [SMILES: O=C1CSc2ncsc2N1Cc1cccc(C(F)(F)F)c1] |

-continued

| Compound number | Structure |
|---|---|
| II-3 | 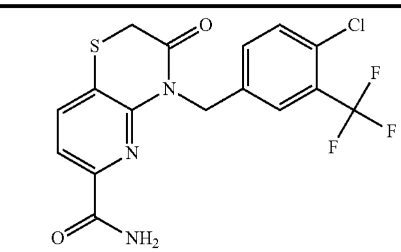 |
| II-4 | 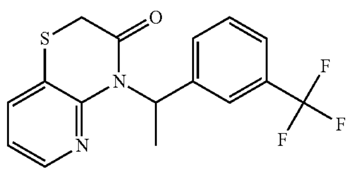 [SMILES: CC(c1cccc(C(F)(F)F)c1)N1C(=O)CSc2cccnc21] |
| II-5 | 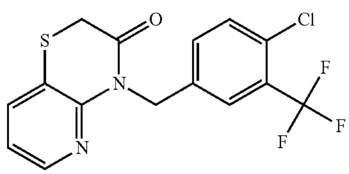 [SMILES: O=C1CSc2cccnc2N1Cc1ccc(Cl)c(C(F)(F)F)c1] |
| II-6 | 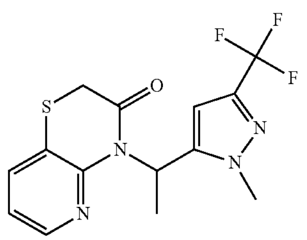 [SMILES: CC(c1cc(C(F)(F)F)nn1C)N1C(=O)CSc2cccnc21] |
| II-7 | 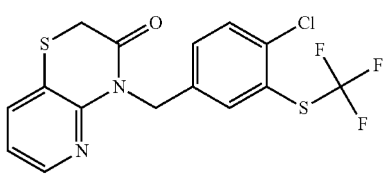 [SMILES: O=C1CSc2cccnc2N1Cc1ccc(Cl)c(SC(F)(F)F)c1] |
| II-8 | 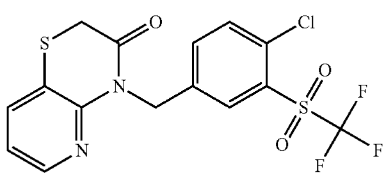 [SMILES: O=C1CSc2cccnc2N1Cc1ccc(Cl)c(S(=O)(=O)C(F)(F)F)c1] |
| II-9 | 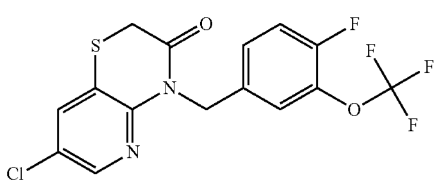 [SMILES: O=C1CSc2cc(Cl)cnc2N1Cc1ccc(F)c(OC(F)(F)F)c1] |
| II-10 | 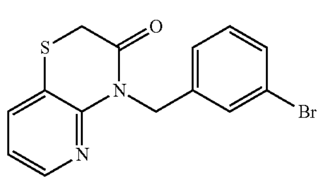 [SMILES: O=C1CSc2cccnc2N1Cc1cccc(Br)c1] |

-continued

| Compound number | Structure |
|---|---|
| II-11 | 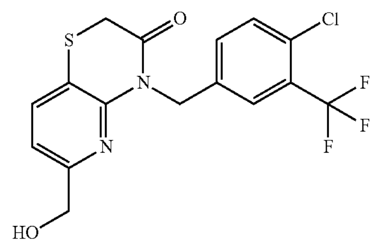 [SMILES: O=C1CSc2ccc(CO)nc2N1Cc1ccc(Cl)c(C(F)(F)F)c1] |
| II-12 | 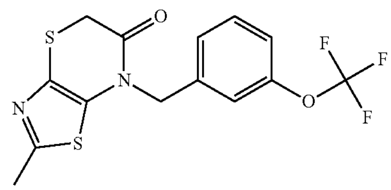 |
| II-13 | 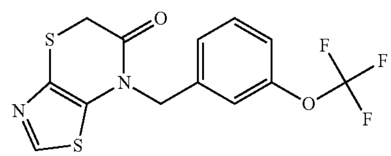 [SMILES: O=C1CSc2ncsc2N1Cc1cccc(OC(F)(F)F)c1] |
| II-14 | 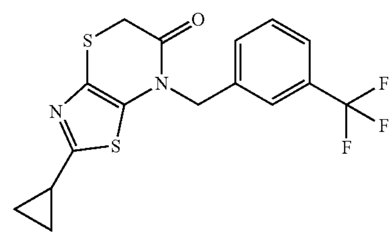 [SMILES: O=C1CSc2nc(C3CC3)sc2N1Cc1cccc(C(F)(F)F)c1] |
| II-15 | 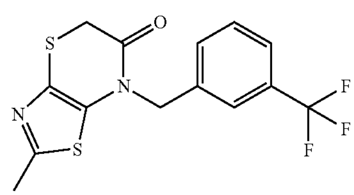 [SMILES: Cc1nc2c(s1)N(Cc1cccc(C(F)(F)F)c1)C(=O)CS2] |
| II-16 | 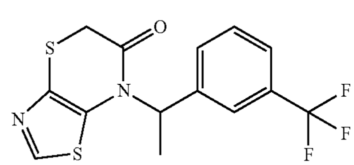 [SMILES: CC(c1cccc(C(F)(F)F)c1)N1C(=O)CSc2ncsc21] |
| II-17 | 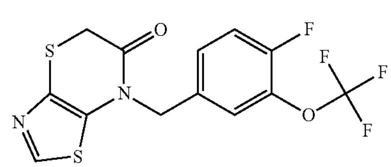 [SMILES: O=C1CSc2ncsc2N1Cc1ccc(F)c(OC(F)(F)F)c1] |

| Compound number | Structure |
|---|---|
| II-18 | 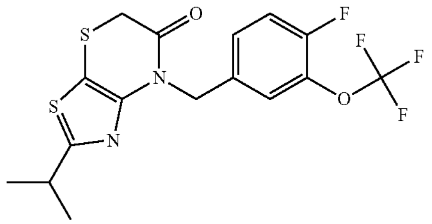 |
| II-19 | 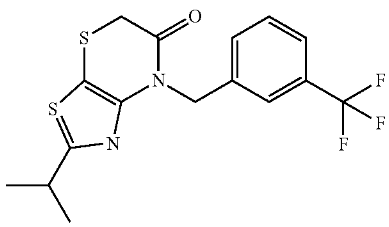 |
| II-20 | 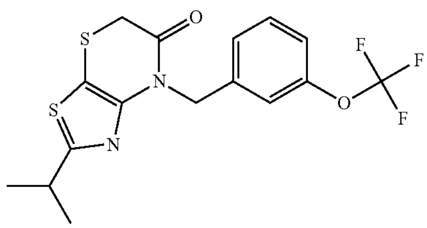 |
| II-21 | 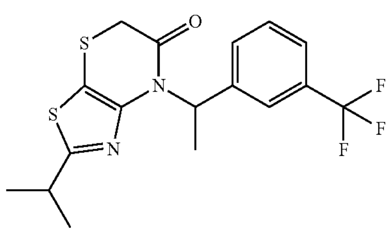 [SMILES: CC(C)c1nc2c(s1)SCC(=O)N2C(C)c1cccc(C(F)(F)F)c1] |
| II-22 | 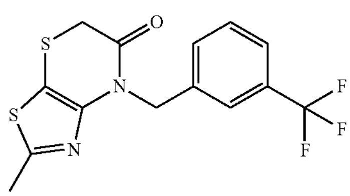 [SMILES: Cc1nc2c(s1)SCC(=O)N2Cc1cccc(C(F)(F)F)c1] |

| Compound number | Structure |
|---|---|
| II-23 | and | or a pharmaceutically acceptable salt thereof.

25. A pharmaceutical composition comprising a therapeutically effective amount of a compound according to claim 1 and one or more pharmaceutically acceptable carriers and/or adjuvants.

26. A method of treating a disease chosen from rheumatoid arthritis, psoriasis, atherosclerosis, systemic lupus erythematosus, Crohn's disease, ulcerative colitis, multiple sclerosis, scleroderma, glomerulonephritis, chronic obstructive pulmonary disease, asthma, inflammatory bowel disease, graft versus host disease, Alzheimer's disease, chronic kidney disease, type 1 and type 2 diabetes, lymphomas, leukemias, osteoporosis, sickle cell disease, restenosis, periodontal disease, resterosis, renal fibrosis, lung fibrosis and liver fibrosis, comprising administering to a patient a therapeutically effective amount of a compound according to claim 1.

27. A pharmaceutical composition comprising a therapeutically effective amount of a compound according to claim 16 and one or more pharmaceutically acceptable carriers and/or adjuvants.

28. A method of treating a disease chosen from rheumatoid arthritis, psoriasis, atherosclerosis, systemic lupus erythematosus, Crohn's disease, ulcerative colitis, multiple sclerosis, scleroderma, glomerulonephritis, chronic obstructive pulmonary disease, asthma, inflammatory bowel disease, graft versus host disease, Alzheimer's disease, chronic kidney disease, type 1 and type 2 diabetes, lymphomas, leukemias, osteoporosis, sickle cell disease, restenosis, periodontal disease, resterosis, renal fiborsis, lung fibrosis and liver fibrosis, comprising administering to a patient a therapeutically effective amount of a compound according to claim 16.

\* \* \* \* \*